US012702319B2

(12) United States Patent
Gopinathan et al.

(10) Patent No.: US 12,702,319 B2
(45) Date of Patent: Aug. 11, 2026

(54) MULTI-SENSOR DEVICE FOR MONITORING HEALTH

(71) Applicant: Analog Devices, Inc., Wilmington, MA (US)

(72) Inventors: Venugopal Gopinathan, Boston, MA (US); James Doscher, Exeter, NH (US); Tony J. Akl, Bedford, MA (US)

(73) Assignee: Analog Devices, Inc., Wilmington, MA (US)

( * ) Notice: Subject to any disclaimer, the term of this patent is extended or adjusted under 35 U.S.C. 154(b) by 81 days.

(21) Appl. No.: 16/478,848

(22) PCT Filed: Jan. 24, 2018

(86) PCT No.: PCT/US2018/015067
§ 371 (c)(1),
(2) Date: Jul. 18, 2019

(87) PCT Pub. No.: WO2018/140509
PCT Pub. Date: Aug. 2, 2018

(65) Prior Publication Data
US 2020/0054238 A1 Feb. 20, 2020

Related U.S. Application Data

(60) Provisional application No. 62/449,741, filed on Jan. 24, 2017.

(51) Int. Cl.
*A61B 5/0535* (2021.01)
*A61B 5/00* (2006.01)
(Continued)

(52) U.S. Cl.
CPC .......... *A61B 5/0535* (2013.01); *A61B 5/0205* (2013.01); *A61B 5/332* (2021.01);
(Continued)

(58) Field of Classification Search
CPC ..... A61B 5/0535; A61B 5/332; A61B 5/0205; A61B 5/6823; A61B 5/6831; A61B 5/684;
(Continued)

(56) References Cited

U.S. PATENT DOCUMENTS 3,874,368 A * 4/1975 Asrican ................ A61B 5/7239 600/526
4,289,142 A 9/1981 Kearns
(Continued)

FOREIGN PATENT DOCUMENTS

CN 103370004 A 10/2013
CN 103976737 A 8/2014
(Continued)

OTHER PUBLICATIONS

Spooner AJ, et al. Head-of-bed elevation improves end-expiratory lung volumes in mechanically ventilated subjects: a prospective observational study. Respir Care 2014;59(10):1583-1589. (Year: 2014).*
(Continued)

*Primary Examiner* — Alex M Valvis
*Assistant Examiner* — Justin Xu
(74) *Attorney, Agent, or Firm* — ArentFox Schiff LLP

(57) ABSTRACT

Devices, systems, and methods for non-invasively detecting and monitoring medical conditions using multiple modalities of sensing include at least two electrodes configured to be positioned on a subject, an acoustic sensor configured to be positioned on a subject, a thoracic impedance measurement module connected to the electrodes, for measuring a first impedance between the electrodes, and a heart acoustic measurement module connected to the acoustic sensor, for detecting and measuring a heart sound from the acoustic sensor.

19 Claims, 14 Drawing Sheets

(51) Int. Cl.

| | |
|---|---|
| ***A61B 5/0205*** | (2006.01) |
| ***A61B 5/053*** | (2021.01) |
| ***A61B 5/085*** | (2006.01) |
| ***A61B 5/332*** | (2021.01) |
| ***A61B 7/04*** | (2006.01) |
| *A61B 5/08* | (2006.01) |
| *A61B 5/087* | (2006.01) |
| *A61B 5/113* | (2006.01) |

(52) U.S. Cl.
CPC .......... *A61B 5/6823* (2013.01); *A61B 5/6831* (2013.01); *A61B 5/684* (2013.01)

(58) Field of Classification Search
CPC ..... A61B 5/085; A61B 5/1135; A61B 5/0816; A61B 5/087; A61B 7/04; A61B 5/053
See application file for complete search history.

(56) References Cited

U.S. PATENT DOCUMENTS 4,690,152 A 9/1987 Juncosa
4,917,099 A 4/1990 Stice
5,020,541 A 6/1991 Marriott
5,477,867 A 12/1995 Balkanyi
6,007,532 A 12/1999 Netherly
6,117,077 A 9/2000 Del et al.
D443,063 S 5/2001 Pisani et al.
D445,507 S 7/2001 Pisani et al.
6,456,872 B1 9/2002 Faisandier
6,847,836 B1 1/2005 Sujdak
7,070,568 B1 7/2006 Koh
7,077,810 B2 7/2006 Lange et al.
7,226,422 B2 6/2007 Hatlestsad et al.
D598,110 S 8/2009 Phillips et al.
D639,437 S 6/2011 Bishay et al.
7,972,276 B1 * 7/2011 Min .................... A61B 5/0538 607/19
7,979,115 B2 7/2011 Stahmann et al.
8,140,154 B2 3/2012 Donnelley et al.
8,328,718 B2 12/2012 Tran
8,369,936 B2 2/2013 Farringdon et al.
D682,439 S 5/2013 Olson et al.
8,483,817 B2 7/2013 Bjorling
D690,021 S 9/2013 Olson et al.
D690,824 S 10/2013 Olson et al.
8,626,262 B2 1/2014 McGusty et al.
D702,356 S 4/2014 Vosch et al.
8,700,118 B2 4/2014 Oster et al.
8,831,898 B2 9/2014 Pinter et al.
D718,458 S 11/2014 Vosch et al.
8,892,196 B2 11/2014 Chang
D719,660 S 12/2014 Vosch et al.
D744,659 S 12/2015 Bishay et al.
D761,436 S 7/2016 Fogarty et al.
D766,447 S 9/2016 Bishay et al.
9,579,060 B1 2/2017 Lisy et al.
D855,191 S 7/2019 Hong et al.
D860,465 S 9/2019 Lovell et al.
D861,179 S 9/2019 Kurachi et al.
D864,400 S 10/2019 Benedikter
10,548,484 B2 2/2020 Brunner et al.
D886,303 S 6/2020 Huang et al.
D890,347 S 7/2020 Chang et al.
D905,858 S 12/2020 Lovell et al.
D914,218 S 3/2021 Govari et al.
10,959,634 B2 3/2021 Varadan et al.
11,047,821 B2 6/2021 Ano et al.
D932,019 S 9/2021 Royea
D932,637 S 10/2021 Hsu
D939,710 S 12/2021 Heikkil
D940,881 S 1/2022 Hadley et al.
D967,433 S 10/2022 Al-Ali et al.
D969,328 S 11/2022 Sun
D970,018 S 11/2022 Soosalu et al.
D972,150 S 12/2022 Kale et al.
D972,736 S 12/2022 Cadena, III
D981,571 S 3/2023 Keeman et al.
D997,938 S 9/2023 Akl et al.
D1,030,071 S 6/2024 Huang et al.
D1,052,089 S 11/2024 Sibal et al.
D1,057,167 S 1/2025 Zhuang
D1,077,219 S 5/2025 Hagerty et al.
D1,090,858 S 8/2025 Akl et al.
D1,094,366 S 9/2025 Akl et al.
2003/0100843 A1 5/2003 Hoffman
2004/0102712 A1 5/2004 Belalcazar et al.
2004/0122485 A1 6/2004 Stahmann et al.
2004/0134496 A1 7/2004 Cho et al.
2005/0101875 A1 5/2005 Semler et al.
2005/0113661 A1 5/2005 Nazeri et al.
2006/0064029 A1 3/2006 Arad
2006/0247739 A1 * 11/2006 Wahlstrand ............ A61B 5/053 607/60
2006/0264776 A1 11/2006 Stahmann et al.
2007/0010758 A1 1/2007 Matthiessen et al.
2007/0073168 A1 3/2007 Zhang et al.
2007/0156061 A1 * 7/2007 Hess .................... A61B 5/0538 600/547
2007/0194776 A1 8/2007 Bossche
2007/0276270 A1 11/2007 Tran
2008/0001735 A1 1/2008 Tran
2008/0004904 A1 1/2008 Tran
2008/0274316 A1 11/2008 Griffith et al.
2008/0275316 A1 11/2008 Fink et al.
2009/0069708 A1 * 3/2009 Hatlestad ............... A61B 5/416 600/547
2009/0118626 A1 5/2009 Moon et al.
2009/0326600 A1 12/2009 Kracker
2010/0004548 A1 1/2010 Rytky
2010/0298899 A1 11/2010 Donnelly et al.
2010/0305633 A1 12/2010 Aziz
2010/0331713 A1 12/2010 Ostrow
2011/0001497 A1 1/2011 Chetelat et al.
2011/0009753 A1 1/2011 Zhang et al.
2011/0061647 A1 3/2011 Stahmann et al.
2011/0204971 A1 8/2011 Chang et al.
2011/0208083 A1 * 8/2011 Gutfinger ............... A61B 5/341 600/547
2011/0237904 A1 9/2011 Kim
2011/0237922 A1 9/2011 Parker et al.
2011/0251817 A1 10/2011 Burns et al.
2011/0257554 A1 * 10/2011 Banet ................... A61B 5/0809 600/536
2012/0070707 A1 3/2012 Kim
2013/0069780 A1 3/2013 Tran et al.
2013/0108995 A1 5/2013 Depasqua et al.
2013/0116578 A1 5/2013 An et al.
2013/0172691 A1 7/2013 Tran
2013/0190577 A1 7/2013 Brunner et al.
2013/0338724 A1 12/2013 Joo et al.
2014/0051962 A1 2/2014 Krusor et al.
2014/0121257 A1 5/2014 Simpson, Jr.
2014/0184422 A1 7/2014 Mensinger et al.
2014/0206948 A1 7/2014 Romem
2014/0206977 A1 7/2014 Bahney et al.
2014/0266375 A1 9/2014 Feldman et al.
2014/0352023 A1 12/2014 Mordecai et al.
2014/0378849 A1 12/2014 Krimsky et al.
2015/0068069 A1 3/2015 Tran et al.
2015/0160185 A1 6/2015 Just et al.
2016/0022164 A1 1/2016 Brockway et al.
2016/0066812 A1 * 3/2016 Cheng .................. A61B 5/0533 600/390
2016/0135715 A1 5/2016 Seppäet al.
2016/0195484 A1 7/2016 Emery
2016/0275776 A1 9/2016 Shen et al.
2016/0287174 A1 10/2016 Joseph
2017/0281095 A1 10/2017 An et al.
2018/0070824 A1 3/2018 Cronin et al.
2018/0116626 A1 5/2018 Darbari et al.
2018/0309096 A1 10/2018 Kim et al.
2018/0325407 A1 11/2018 Varadan et al.
2019/0021633 A1 1/2019 Wang et al.

(56) References Cited

U.S. PATENT DOCUMENTS

| | | | |
|---|---|---|---|
| 2019/0022400 A1* | 1/2019 | Kumar ................ | A61N 1/3904 |
| 2019/0059777 A1 | 2/2019 | Aga et al. | |
| 2019/0167176 A1 | 6/2019 | Annoni et al. | |
| 2019/0223782 A1 | 7/2019 | Wen et al. | |
| 2020/0038708 A1 | 2/2020 | Cheu et al. | |
| 2020/0196878 A1 | 6/2020 | Bentzion et al. | |
| 2020/0329977 A1 | 10/2020 | Freeman et al. | |
| 2020/0397315 A1 | 12/2020 | Raj et al. | |
| 2021/0153837 A1 | 5/2021 | Jones | |
| 2021/0333759 A1 | 10/2021 | Vasavada et al. | |
| 2021/0386318 A1 | 12/2021 | Rahman et al. | |
| 2021/0401317 A1 | 12/2021 | Chtelat | |
| 2022/0031253 A1 | 2/2022 | Burnes et al. | |
| 2022/0233241 A1 | 7/2022 | Shelton, IV et al. | |
| 2022/0344025 A1 | 10/2022 | Bort et al. | |
| 2023/0061046 A1 | 3/2023 | Lim et al. | |
| 2023/0200710 A1 | 6/2023 | Thakur et al. | |

FOREIGN PATENT DOCUMENTS

| | | |
|---|---|---|
| CN | 104138259 A | 11/2014 |
| CN | 107957542 A | 4/2018 |
| CN | 108209914 A | 6/2018 |
| CN | 105286909 | 2/2019 |
| EP | 1923952 A1 | 5/2008 |
| EP | 3153099 A1 | 4/2017 |
| EP | 2603138 B1 | 11/2017 |
| GB | 6392893 | 10/2024 |
| JP | 2007-027103 A | 2/2007 |
| JP | 2010-282824 A | 12/2010 |
| JP | 2012-074265 A | 4/2012 |
| JP | 2013/540523 | 11/2013 |
| JP | 2016-517324 A | 6/2016 |
| JP | 2016/154864 | 9/2016 |
| JP | 2019-530550 A | 10/2019 |
| JP | 2023-177220 A | 12/2023 |
| KR | 10-2009-0124140 A | 12/2009 |
| KR | 10-2513594 B1 | 3/2023 |
| TW | 201626950 A | 8/2016 |
| WO | 00/07013 A2 | 2/2000 |
| WO | 2005/044090 A2 | 5/2005 |
| WO | 2009/148425 A1 | 12/2009 |
| WO | 2012/021900 | 2/2012 |
| WO | 2013/176861 A1 | 11/2013 |
| WO | 2014/021883 A1 | 2/2014 |
| WO | 2014/145487 A1 | 9/2014 |
| WO | 2016/040879 | 3/2016 |
| WO | 2017214198 A1 | 12/2017 |
| WO | 2018/140509 A1 | 8/2018 |
| WO | 2018/217017 A2 | 11/2018 |
| WO | 2020/047607 A1 | 3/2020 |
| WO | 2020/148280 A2 | 7/2020 |
| WO | 2021/110937 A1 | 6/2021 |

OTHER PUBLICATIONS

Kubota S, et al. Effects of trunk posture in Fowlers position on hemodynamics. Autonom Neurosci Basic Clin 2015; 189: 56-59. (Year: 2015).*

ISR-WO issued in PCT Patent Application Serial No. PCT/US2018/015067 dated May 8, 2018, 13 pages.

English Abstract of CN105286909, 12 pages.

Office Action issued in JP Patent Application Serial No. 2019-539968 dated Mar. 3, 2021, 5 pages—no EN translation.

EP Search Report issued in EP Patent Application Serial No. 18744790.0 dated Aug. 14, 2020, 9 pages.

Bera, Tushar Kanti, "Bioelectrical Impedance Methods for Noninvasive Health Monitoring: A Review," Journal of Medical Engineering, 2014, vol. 2014, Article ID 381251, 28 pages.

Office Action in IL267944, dated Feb. 26, 2023, 5 pages.

International Search Report and Written Opinion for International Application No. PCT/EP2020/050813, mailed Jul. 21, 2020, 26 pages.

International Preliminary Report on Patentability for International Application No. PCT/EP2020/050813, mailed Jun. 16, 2021, 15 pages.

Bera, T. K., "Bioelectrical Impedance and The Frequency Dependent Current Conduction Through Biological Tissues: A Short Review," IOP Conference Series: Materials Science and Engineering, 012005, vol. 331, 2018, pp. 1-9.

Blanco-Almazan et al., "Wearable Bioimpedance Measurement for Respiratory Monitoring During Inspiratory Loading", IEEE Access, vol. 7, Jul. 5, 2019, pp. 89487-89496.

Broeders, Jan-Hein, "Wearable Electronic Device Monitor Vital Signs, Activity Level, and More", Analog Dialogue, vol. 48, Dec. 2014, pp. 1-6.

Daic, "Medtronic Launches SEEQ Wearable Cardiac Monitoring System in United States", Medtronic Monitor, Avaiable online at: <https://www.discardiology.com/product/medtronic-launches-seeq-wearable-cardiac-monitoring-system-united-states>, Oct. 7, 2014, pp. 1-6.

Demidenko, E., "An Analytic Solution to the Homogeneous EIT Problem on the 2d Disk and Its Application to Estimation of Electrode Contact Impedances", NIH Public Access, Author Manuscript, Physiological Measurement, PMC, Sep. 1, 2012, pp. 1-24.

Extended European Search Report recevied for European Patent Application No. 24194357.0, mailed on Jan. 23, 2025, 9 pages.

Extended European Search Report received for European Patent Application No. 25154191.8, mailed on Nov. 17, 2025, 12 pages.

Extended European Search Report received for European Patent Application No. 25154192.6, mailed on Jun. 30, 2025, 9 pages.

Grenvik et al., "Impedance Pneumography: Comparison between Chest Impedance Changes and Respiratory Volumes in II Health Voultuneers", Chest, vol. 62, No. 4, Oct. 1972, pp. 439-443.

Hamilton et al., "Impedance Measurement of Tidal Volume and Ventilation", Journal of Applied Physilogy, vol. 20, No. 3, May 1965, pp. 565-568.

International Preliminary Report on Patentability received for PCT Patent Application No. PCT/EP2020/050545, mailed on Jul. 22, 2021, 11 pages.

International Preliminary Report on Patentability received for PCT Patent Application No. PCT/EP21/082219, mailed on Jun. 1, 2023, 9 pages.

International Preliminary Report on Patentability received for PCT Patent Application No. PCT/US2018/015067, mailed on AUg. 8, 2019, 7 pages.

International Search Report and Written Opinion received for PCT Patent Application No. PCT/EP2020/050545, mailed Mar. 31, 2020, 13 pages.

International Search Report and Written Opinion received for PCT Patent Application No. PCT/EP2021/082219, mailed on Mar. 31, 2022, 11 pages.

International Search Report and Written Opinion received for PCT Patent Application No. PCT/EP2025/055429, mailed on May 6, 2025, 14 pages.

International Search Report and Written Opinion received for PCT Patent Application No. PCT/US2025/027751, mailed on Jul. 28, 2025, 14 pages.

Mlynczak et al., "Motion Artifact Detection in Respiratory Signals based on Teager Energy Operator and Accelermetor Signals", IFMBE Proceedings, vol. 65, 2017, pp. 45-48.

Partial European Search Report received for European Patent Application No. 25154190.0, mailed on Jun. 30, 2025, 12 pages.

Partial European Search Report received for European Patent Application No. 25154191.8, mailed on Jun. 30, 2025, 14 Pages.

Seppea et al., "Assessment of Pumonary Flow Using Impedance Pneumography", IEEE Transaction on Biomedical Engineering, vol. 57, No. 9, Sep. 2010, pp. 22777-2285.

Seppa et al., "Novel Electrode Configuration for Highly Linear Impedance Penumography", Journal of Biomed Tech., vol. 58, No. 1, Feb. 2013, pp. 35-38.

Design U.S. Appl. No. 29/901,773 filed on Sep. 5, 2023.

Quad Industries, "Smart Health Patches to Run Smart", Available from the Internet URL: <https://www.quad-ind.com/smart-health-patches-to-run-smart/>, 2026, 6 pages.

(56) References Cited

OTHER PUBLICATIONS

Schieszer, John, "Wearable Medical Monitoring Devices: The Innovation Continues", Available from the internet URL: <https://www.renalandurologynews.com/features/wearable-medical-monitoring-devices-the-innovation-continues/>Oct. 31, 2022, 3 pages.

* cited by examiner

TO/FROM 106
(FIG. 1)
TO/FROM 110
(FIG. 1)
116
122
210
TRANSMITTER/
RECEIVER
204
DATA STORAGE
206
MEMORY
208
PROCESSOR
202
DATA ANALYZER
226
DATA FUSION/
DECISION ENGINE
228
102
MULTI-MODALITY SENSING AND
MEASUREMENT MODULES
112
THORACIC IMPEDANCE
MEASUREMENTS
212
ELECTROCARDIOGRAM
MEASUREMENTS
214
BREATH RATE
MEASUREMENTS
216
TIDAL VOLUME
MEASUREMENTS
218
HEART SOUNDS-BASED
MEASUREMENTS
220
PULSE OXIMETRY
MEASUREMENTS
222
ELECTRODE/SENSOR
CONNECTION
SWITCHING CIRCUITRY
224
TO/FROM
ELECTRODES/
SENSORS
114a - 114d
(FIG. 1)

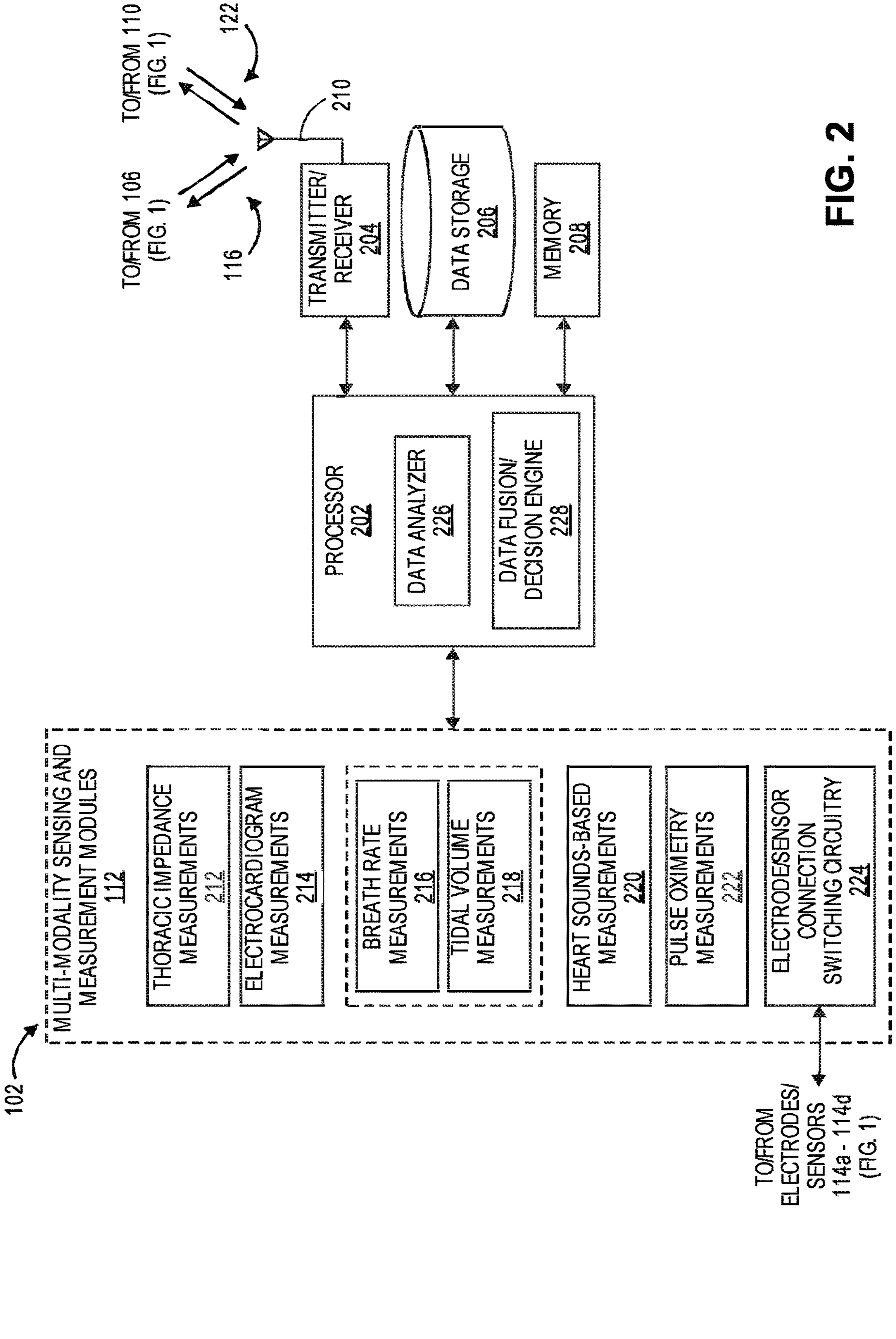

FIG. 2

*Medical classifications of heart failure*

MULTI-SENSOR DEVICE FOR MONITORING HEALTH

CROSS-REFERENCE TO RELATED APPLICATION

This Application claims the benefit of priority under 35 U.S.C. § 119 of U.S. Application Ser. No. 62/449,741 filed Jan. 24, 2017, and entitled "Congestive Heart Failure (CHF) Management: Multi-Sensor Modality". The disclosure of the prior Application is considered part of and is incorporated by reference in the disclosure of this Application.

FIELD OF THE DISCLOSURE

The present application relates generally to systems, apparatus, and methods of managing medical or health conditions in human subjects, and more specifically to systems, apparatus, and methods of non-invasively detecting and monitoring medical or health conditions such as congestive heart failure (CHF) and Chronic Obstructive Pulmonary Disease (COPD) conditions in human subjects that employ multiple modalities of sensing.

BACKGROUND

In human subjects, congestive heart failure (CHF) is a known cardiac condition in which damaged heart muscle loses its ability to pump sufficient amounts of blood to meet the body's demands. In the early stages of CHF, such an inability to pump sufficient amounts of blood may occur only while a human subject exercises. However, in more advanced stages of CHF, such an inability to pump sufficient amounts of blood may occur even while the human subject is at rest. CHF is one of the most commonly diagnosed cardiac conditions in hospital patients over the age of 65, and one of the most frequent reasons for such patients' readmission to hospitals in a time duration of 30 days. In recent years, 30-day hospital readmission expenses for CHF have increased to $1.8 billion per year, with approximately $13,000 being allotted for each readmission at a 25% readmission rate, Some of the reasons for such patients' readmission to hospitals can include, but are not limited to, (1) patient non-compliance with regard to diet and medication, which can result in excess fluid in the lungs or extreme dehydration, (2) incomplete titration of medication dosages, which often need to be modified as a patient moves from the hospital environment back to his or her home, and (3) atrial fibrillation, which can onset after the patient's discharge from the hospital.

Management of CHF in patients following discharge from the hospital has traditionally focused on monitoring the patients' fluid retention using sensors incorporated in implantable cardiac devices, such as implantable cardioverter defibrillators (LCDs), cardiac resynchronization therapy-defibrillators (CRT-Ds), or pacemakers. Such implantable cardiac devices can detect developing pulmonary congestion in a patient by measuring the patient's thoracic fluid impedance. For example, an implantable cardiac device such as an ICD, CRT-D, or pacemaker can be configured to pass an electrical current across a patient's lung, and to measure the resulting intra-thoracic impedance. As the patient's thoracic fluid accumulates during pulmonary congestion, conductance across the patient's lung increases, causing a corresponding decrease in impedance indicative of the level of thoracic fluid accumulation. Such implantable cardiac devices can also be interrogated by hospital clinicians, allowing the hospital clinicians to monitor the patient's fluid status and to receive early warnings of changes that may signal an impending fluid overload. Based on the patient's monitored fluid status, the hospital clinicians may then determine whether or not it would be appropriate to readmit the patient to the hospital for further monitoring and/or treatment.

SUMMARY OF THE DISCLOSURE

Systems, methods, and devices for non-invasively detecting and monitoring medical conditions are disclosed. The medical condition may be one of Chronic Obstructive Pulmonary Disease (COPD). According to one implementation, a device for non-invasively detecting and monitoring medical conditions using multiple modalities of sensing, comprises at least two electrodes configured to be positioned on a subject, an acoustic sensor configured to be positioned on a subject, a thoracic impedance measurement module connected to the at least two electrodes, for measuring a first impedance between the at least two electrodes, and a heart acoustic measurement module connected to the acoustic sensor, for detecting and measuring a heart sound from the acoustic sensor. In some implementations, the heart sound is an S3 heart sound. In some implementations, the heart sound is an S4 heart sound. In various implementations, the acoustic sensor is at least one of an ultrasound sensor and a piezoelectric microphone sensor. In some implementations, the at least two electrodes include two electrode pairs, and each electrode pair includes a force electrode and a sense electrode. The force electrode is configured to apply current to the subject and the sense electrode is configured to sense changes caused by the applied current. The changes may include changes in measured voltage.

In some implementations, the device includes a sensor for determining an orientation of the device. In one implementation, the thoracic impedance measurement module measures the first impedance when the device is in a first orientation, and measures a second impedance between the at least two of the surface sensors when the device is in a second orientation. In one example, a first orientation indicates that the device is approximately horizontal, and the second orientation indicates that the device is approximately vertical. In another example, a first orientation indicates that the device is approximately horizontal, and the second orientation indicates that the device is positioned at an angle of between about 30 degrees and about 90 degrees with respect to the horizontal plane. In another example, a first orientation indicates that the device is approximately horizontal, and the second orientation indicates that the device is positioned at an angle greater than about 30 degrees with respect to the horizontal plane. In one example, the second orientation indicates that the device is in a Fowler's position. In some implementations, the thoracic impedance measurement module automatically measures the first impedance at regular intervals.

In one implementation, the device further comprises an electrocardiogram measurement module, connected to the electrodes, for measuring electrical activity between the electrodes.

According to one implementation, a system for non-invasively detecting and monitoring medical conditions using multiple modalities of sensing, comprises a device positioned on a subject having a plurality of surface sensors and a plurality of sensing modules connected to the plurality of surface sensors, configured to gather multi-modality sensing data, and a data analyzer operative to perform at least one of data analysis, data trending, and data reduction of the multi-modality sensing data. The multi-modality sensing data includes a first impedance between at least two of the surface sensors, and heart sounds from at least one of the plurality of surface sensors. In various implementations, the surface sensors include at least one of electrodes, heart sounds sensors, ultrasound sensors, and photoplethysmography sensors.

In some implementations, the system further includes a data decision engine configured to combine at least some of the multi-modality sensing data, wherein the combined multi-modality sensing data indicates a medical condition status of the subject. In some implementations, the system further includes a transceiver configured to transmit the combined multi-modality sensing data over at least one wireless communication path to a cloud for further processing.

In some implementations, the device in the system further comprises a sensor for determining an orientation of the device. In some implementations, the device includes a thoracic impedance measurement module configured to measure the first impedance when the device is in a first orientation and a second impedance between the at least two of the surface sensors when the device is in a second orientation. In some implementations, the device in the system further comprises an electrocardiogram measurement module, connected to the plurality of surface sensors, for measuring electrical activity between at least two of the surface sensors.

According to some implementations, a method for non-invasively detecting and monitoring medical conditions using multiple modalities of sensing comprises transmitting a current transcutaneously from a first electrode positioned on a subject, receiving a current transcutaneously at a second electrode positioned on the subject, measuring a voltage between the first and second electrodes, determining a thoracic impedance at least based on the voltage, receiving an acoustic signal from an acoustic sensor, measuring a heart sound from the acoustic sensor, and transmitting thoracic impedance data and heart sound measurements to a data analyzer configured to perform at least one of data analysis, data trending, and data reduction of the thoracic impedance data and heart sound measurements. In some implementations, the method further comprises measuring electrical activity between the first and second electrodes and producing an electrocardiogram.

In some implementations, the method further comprises determining an orientation of the device. In some implementations, the thoracic impedance is determined when the device is in a first orientation and the method further comprises determining a second impedance measurement between the first and second electrodes when the device is in a second orientation.

In accordance with the present application, systems, apparatus, and methods are disclosed for non-invasively detecting and monitoring medical or health conditions such as congestive heart failure (CHF) conditions in human subjects using multiple modalities of sensing, including, but not limited to, thoracic impedance sensing, electrocardiogram (ECG) sensing, breath rate sensing, tidal volume sensing, heart sounds sensing, pulse oximetry sensing, blood pressure (systolic, diastolic) sensing, cardiac output sensing, etc. The disclosed systems, apparatus, and methods can non-invasively gather and at least partially analyze, trend, and/or reduce data from each modality of sensing, and perform data fusions on some or all of the multi-modality sensing data in order to obtain curated data useful in detecting the onset of CHF in a human subject and/or monitor its severity. The disclosed systems, apparatus, and methods can also transmit such multi-modality sensing data (as well as other information pertaining to the onset and/or severity of the human subject's CHF) either directly over a communications network to the "cloud," or to a smartphone or other communications device, which, in turn, can transmit the multi-modality sensing data and/or other information over the communications network to the cloud. The multi-modality sensing data can also he analyzed, trended, reduced, and/or fused in the cloud to augment or at least partially replace the data analysis, trending, reduction, and/or fusion performed by the disclosed systems, apparatus, and methods. The resulting curated multi-modality sensing data and/or other information may then be remotely downloaded from the cloud by hospital clinicians for monitoring and/or tracking purposes. By non-invasively gathering and analyzing data from multiple modalities of sensing to detect the onset of CHF and/or monitor its severity in human subjects, the disclosed systems, apparatus, and methods can increase the positive detection of potentially problematic CHF conditions while decreasing false positives, which can reduce the number of unnecessary hospital readmissions, shorten hospital stays, and reduce hospital costs.

In certain embodiments, a method of non-invasively detecting and monitoring medical or health conditions such as congestive heart failure (CHF) conditions in human subjects using multiple modalities of sensing includes positioning a non-invasive CHF detection and monitoring device on a human subject such that it makes contact with the human subject's torso and upper chest and neck areas or any other suitable parts or areas of the body, via at least a plurality of surface electrodes and/or one or more sensors such as heart sound sensors, ultrasound sensors, photoplethysmography (PPG) sensors, etc. Once the CHF detection and monitoring device is positioned in contact with the human subject's torso and upper chest and neck areas, a plurality of multi-modality sensing and measurement modules contained in the CHF detection and monitoring device are activated to obtain multi-modality sensing data from the human subject The multi-modality sensing data can include, but are not limited to, one or more of thoracic impedance sensing data, electrocardiogram (ECG) sensing data, breath rate and tidal volume sensing data, heart rate variability/heart sounds-based sensing data, and pulse oximetry sensing data. The multi-modality sensing data are provided to a data analyzer contained in the CHF detection and monitoring device for at least partially analyzing, trending, and/or reducing the data. Next, the analyzed multi-modality sensing data are at least partially fused or combined by a data fusion/decision engine contained in the CHF detection and monitoring device for subsequent use in making one or more inferences about the CHF status of the human subject. The at least partially fused or combined multi-modality sensing data are then transmitted by a transmitter/receiver contained in the CHF detection and monitoring device over one or more wireless communication paths to the cloud for possible further data analysis, trending, reduction, and/or fusion, as well as subsequent remote downloading by hospital clinicians for monitoring and/or tracking purposes.

In certain further embodiments, an apparatus for non-invasively detecting and monitoring medical or health conditions such as CHF conditions in human subjects using multiple modalities of sensing includes a non-invasive CHF detection and monitoring device configured to be positioned on a human subject, thereby making contact with the human subject's torso and upper chest and neck areas or any other suitable parts or areas of the body, via at least a plurality of surface electrodes and/or one or more sensors, such as heart sound sensors, ultrasound sensors, photoplethysmography (PPG) sensors, etc. The CHF detection and monitoring device includes a plurality of multi-modality sensing and measurement modules, a data analyzer, a data fusion/decision engine, and a transmitter/receiver. The plurality of multi-modality sensing and measurement modules are operative to obtain multi-modality sensing data from the human subject, including, but not limited to, one or more of thoracic impedance sensing data, ECG sensing data, breath rate and tidal volume sensing data, heart rate variability/heart sounds-based sensing data, and pulse oximetry sensing data. The data analyzer is operative to perform at least partial data analysis, data trending, and/or data reduction on the multi-modality sensing data. The data fusion/decision engine is operative to at least partially fuse or combine the analyzed multi-modality sensing data for subsequent use in making one or more inferences about the CHF status of the human subject. The transmitter/receiver is operative to transmit the at least partially fused or combined multi-modality sensing data over one or more wireless communication paths to the cloud for possible further data analysis, trending, reduction, and/or fusion, as well as subsequent remote downloading by hospital clinicians for monitoring and/or tracking purposes.

Other features, functions, and aspects of the present application will be evident from the Detailed Description that follows.

BRIEF DESCRIPTION OF THE DRAWINGS

The accompanying drawings, which are incorporated in and constitute a part of the present application, illustrate one or more embodiments described herein, and, together with the Detailed Description, explain these embodiments. In the drawings:

FIG. 2 is a diagram illustrating exemplary functional components of the system of FIG. 1, according to some embodiments of the disclosure.

DETAILED DESCRIPTION

Figure 1:
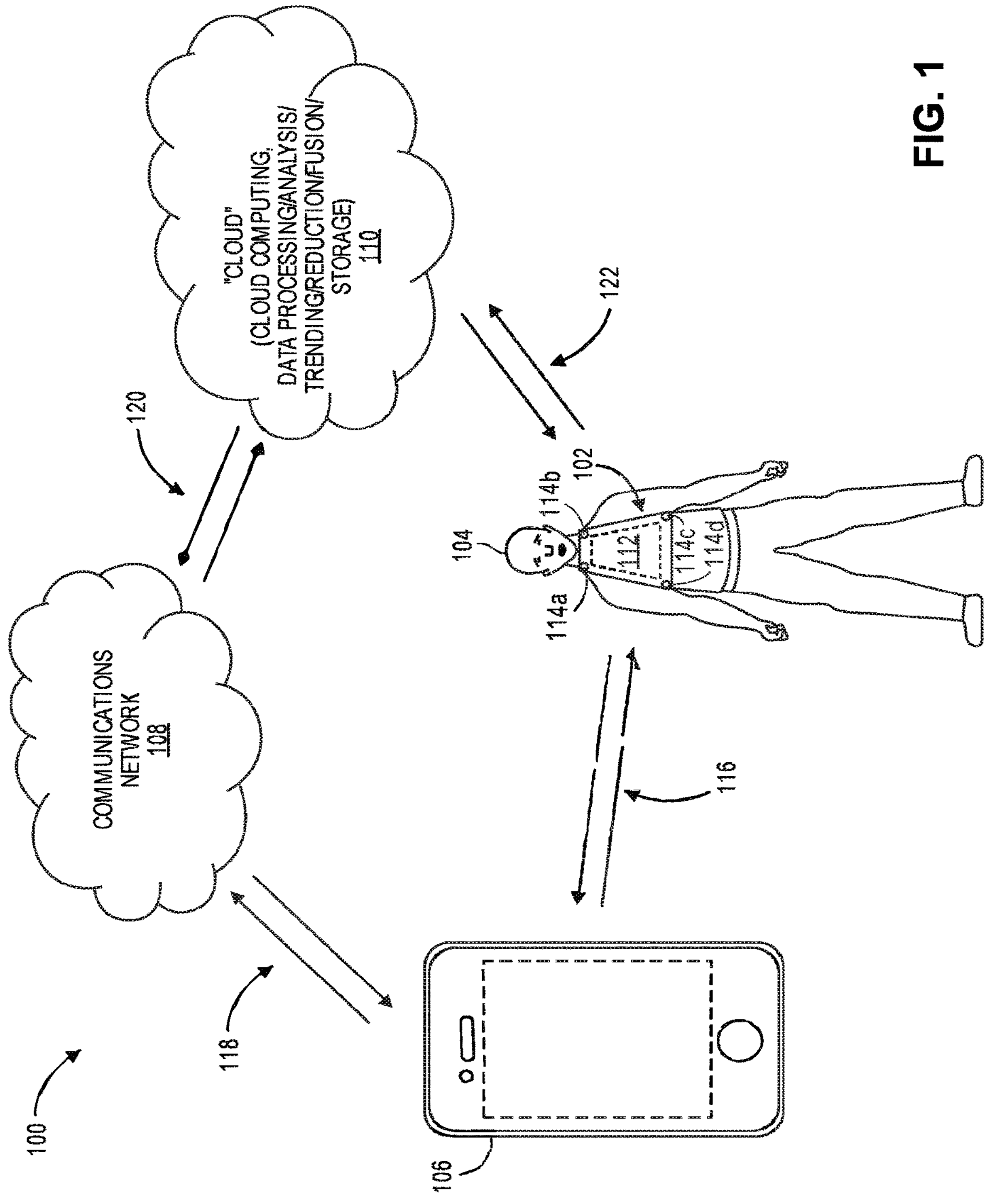
FIG. 1 is a diagram illustrating an environment including an exemplary system for non-invasively detecting and monitoring medical or health conditions in a subject using multiple modalities, according to some embodiments of the disclosure.

Systems, apparatus, and methods are disclosed for non-invasively detecting and monitoring medical or health conditions such as congestive heart failure (CHF) conditions and chronic obstructive pulmonary disease (COPD) conditions in human subjects using multiple modalities of sensing. In particular, a device for non-invasively gathering and analyzing, trending, and/or reducing data from each modality of sensing is disclosed. The device can perform data fusions on some or all of the multi-modality sensing data to obtain curated data useful in detecting the onset of a health condition in a human subject and/or monitor its severity, and transmit such multi-modality sensing data (as well as other information pertaining to the onset and/or severity of the human subject's health condition). The data can be transmitted either directly over a communications network to the "cloud," or to a smartphone or other communications device. A smartphone or other communication device can analyze the data locally, or the smartphone ore other communication device can transmit the multi-modality sensing data and/or other information over the communications network to the cloud. Data transmitted to the cloud can be remotely analyzed, trended, reduced, and/or fused to augment or at least partially replace the data analysis, trending, reduction, and/or fusion performed by the disclosed systems, apparatus, and methods. In some examples, hospital clinicians can remotely download the resulting curated multi-modality sensing data and/or other information from the cloud for monitoring and/or tracking the health status of the human subject.

The disclosed systems, apparatus, and methods for non-invasively detecting and monitoring CHF conditions in human subjects using multiple modalities of sensing can provide improvements over conventional implantable cardiac devices for managing CHF in human subjects, such as implantable cardioverter defibrillators (ICDs), cardiac resynchronization therapy-defibrillators (CRT-Ds), or pacemakers. For example, such conventional implantable cardiac devices typically include one or more sensors configured to provide a single or limited number of sensing modalities, such as a modality for detecting a human subject's fluid retention. However, monitoring and/or tracking the CHF status of a human subject based on just a single or limited number of sensing modalities can often lead to false positives, resulting in unnecessary hospital readmissions that can increase hospital costs. Further, such conventional implantable cardiac devices are generally incapable of analyzing the interrelationship of multi-modality sensing data to obtain positive detection of potentially problematic CHF conditions in human subjects. Moreover, the implantable nature of such conventional cardiac devices can increase surgical risks, as well as the incidence of infection. Additionally, the implantable nature of such conventional cardiac devices limits the availability of the devices to patients, since only patients qualified for the surgery to insert the implant can receive the device.

The disclosed systems, apparatus, and methods for non-invasively detecting and monitoring medical or health conditions such as CHF and COPD conditions in human subjects can non-invasively gather data, and at least partially analyze, trend, and/or reduce data from multiple modalities of sensing. Additionally, the systems, apparatus, and methods can perform data fusions on some or all of the multi-modality sensing data and obtain curated data useful in detecting the onset of CHF and/or COPD, and also useful in monitoring the severity of CHF and/or COPD in human subjects. The disclosed systems, apparatus, and methods thereby increase the positive detection of potentially problematic CHF and COPD conditions while decreasing false positives, which can reduce the number of unnecessary hospital readmissions, shorten hospital stays, and reduce hospital costs. Moreover, the disclosed systems, apparatus, and methods for non-invasively detecting and monitoring CHF and COPD conditions can be implemented in an external device that can be conveniently employed by a human subject following discharge from the hospital, allowing the human subject as well as hospital clinicians to monitor the subject's CHF and/or COPD status with reduced risks from surgery and/or infection.

Worsening heart failure is correlated with changes over time in multiple measurements that can be gathered using the non-invasive systems, apparatus, and methods disclosed herein. In particular, worsening heart failure is correlated with an in increase in amplitude of the S3 heart sound, increasingly rapid and shallow breathing at rest, a decrease in the relative tidal volume (the lung volume representing the volume of air displaced between inhalation and exhalation at rest), and a decrease in thoracic impedance.

FIG. 1 depicts a typical environment 100 in which an illustrative embodiment of an exemplary system 102 for non-invasively detecting and monitoring medical or health conditions such as congestive heart failure (CHF) conditions in human subjects using multiple modalities of sensing may be employed, according to some embodiments of the disclosure. As shown in FIG. 1, the system 102 includes a plurality of multi-modality sensing and measurement modules 112 (see also FIG. 2), and a plurality of surface electrodes/sensors 114*a*-114*d* (e.g., four (4) surface electrodes/sensors, or any other suitable number of surface electrodes/sensors). For example, one or more of the surface electrodes can be implemented as solid-gel surface electrodes, or any other suitable surface electrodes. Further, one or more of the sensors can be implemented as heart sound sensors, ultrasound sensors, photoplethysmography (PPG) sensors, or any other suitable sensors. The system 102 can be configured as a generally triangular-shaped device, or any other suitably shaped device, operative to make contact with one or more of the torso, upper chest, and neck areas, or any other suitable parts or areas of the body, of a human subject 104 via at least the plurality of surface electrodes/sensors 114*a*-114*d*.

In various implementations, the system 102 can have a configuration that allows it to be implemented within a wearable vest-like structure, as multiple patch-like devices, or any other suitable structure or device(s). Various examples of device configurations are shown in FIGS. 3-5 and FIG. 7.

In the typical environment 100, the system 102 is operative to engage in bidirectional communications over wireless communication paths 116 with a smartphone 106, which, in turn, is operative to engage in bidirectional communications over wireless communication paths 118 with a communications network 108 (e.g., the Internet). The smartphone 106 is further operative, via the communications network 108, to engage in bidirectional communications over wireless communication paths 120 with the cloud 110, which can include resources for cloud computing, data processing, data analysis, data trending, data reduction, data fusion, data storage, and other functions. The system 102 is further operative to engage in bidirectional communications over wireless communication paths 122 directly with the cloud 110.

FIG. 2 depicts a detailed view of the system 102 for non-invasively detecting and monitoring medical or health conditions such as CHF and/or COPD conditions in human subjects, according to some embodiments of the disclosure. As shown in FIG. 2, the system 102 includes the plurality of multi-modality sensing and measurement modules 112, a processor 202 and its associated memory 208, a data storage 206 for storing multi-modality sensing data, and a transmitter/receiver 204. The transmitter/receiver 204 can be configured to perform Bluetooth communications, WiFi communications, or any other suitable short-range communications for communicating with the smartphone 106 (see FIG. 1) over the wireless communication paths 116. The transmitter/receiver 204 can be further configured to perform cellular communications or any other suitable long-range communications for communicating with the cloud 110 (see FIG. 1) over the wireless communication paths 122.

In some implementations, the plurality of multi-modality sensing and measurement modules 112 can include, but are not limited to, one or more of a thoracic impedance measurement module 212, an electrocardiogram (ECG) measurement module 214, breath rate and tidal volume measurement modules 216, 218, a heart sounds-based measurement module 220, and a pulse oximetry measurement module 222. In one embodiment, the system 102 can be configured to perform reflective pulse oximetry measurements. In another embodiment, the system 102 can include a finger-pocket device (not shown) for performing finger-based pulse oximetry measurements. The plurality of multi-modality sensing and measurement modules 112 further include electrode/sensor connection switching circuitry 224 for switchably making connections with the plurality of surface electrodes/sensors 114*a*-114*d* shown in FIG. 1.

The processor 202 can include a plurality of processing modules such as a data analyzer 226 and a data fusion/decision engine 228. The transmitter/receiver 204 can include at least one antenna 210 operative to transmit/receive wireless signals such as Bluetooth or WiFi signals over the wireless communications paths 116 to/from the smartphone 106, which can be a Bluetooth or WiFi-enabled smartphone or any other suitable smartphone. The antenna 210 is further operative to transmit/receive wireless signals such as cellular signals over the wireless communications paths 122 to/from the cloud 110.

The operation of the system 102 for non-invasively detecting and monitoring medical or health conditions such as CHF and COPD conditions in human subjects using multiple modalities of sensing will be further understood with reference to the following illustrative example, as well as FIGS. 1 and 2. In this illustrative example, at fixed times each day for a predetermined number of days (e.g., twice a clay) while the human subject 104 is in a supine or upright position, the human subject 104 (see FIG. 1) or a human assistant positions the system 102 configured as the generally triangular-shaped device (or any other suitably shaped device) such that it makes contact with one or more of the subject's torso and upper chest and neck areas (or any other suitable parts or areas of the body) via the plurality of surface electrodes/sensors 114*a*-114*d*.

Having positioned the system 102 in contact with the human subject's torso and/or upper chest and/or neck areas, the plurality of multi-modality sensing and measurement modules 112 can be activated to gather, collect, sense, measure, or otherwise obtain multi-modality sensing data from the human subject 104. For example, the thoracic impedance measurement module 212 can perform thoracic impedance sensing using multiple vectors to obtain a measure of the human subject's thoracic fluid impedance, as well as trends for obtaining a localization of fluid congestion in the lungs. To that end, the thoracic impedance measurement module 212 can apply, via the electrode/sensor connection switching circuitry 224, a suitable high frequency, low amplitude current between two or more of the surface electrodes 114*a*-114*d*. In one example, the current is applied between two electrodes 114*a*-114*d* at the neck and thorax of the human subject, such as the surface electrode pair 114*a*, 114*b*. The thoracic impedance measurement module 212 obtains, via the electrode/sensor connection switching circuitry 224, a thoracic impedance signal by measuring the potential difference between two of the surface electrodes 114*a*-114*d*. In some examples, the high frequency, low amplitude current applied between the surface electrodes 114*a*-114*d* has a frequency between about 50 kHz and about 100 kHz and has an amplitude between about 1 $mA_{rms}$ and 4 $mA_{rms}$. In other examples, the current has a frequency below about 50 kHz or above about 100 kHz. In some examples, the current has a frequency of between about 20 kHz and about 200 kHz, or between about 20 kHz and about 1 MHz.

In some implementations, the thoracic impedance measurement module 212 uses measurements obtained from two pairs of surface electrodes. In one implementation, four electrodes are used for impedance measurements. The four electrodes include two force electrodes and two sense electrodes, with each force electrode paired with a sense electrode. Each group of four electrodes can resolve a vector in space to localize observed changes. There are two of the four electrodes on each side of a vector. In particular, on each side of a vector, there is a force electrode and a sense electrode. The force electrode applies (or injects) current into the body (or receives current injected into the body). The sense electrode measures the disturbance caused by the current applied into the body by the force electrode. In various implementations, the sense electrodes of the vector sense current and/or voltage drop caused by the injection of a current into the body by the force electrodes through application of a voltage and/or current. Since voltage and current are related to impedance ($V=Z*i$), to measure impedance Z, a known current i can be applied, and the subsequent voltage drop V can be measured, and Z can be calculated using the known current i and measured change in voltage V. According to various implementations, the properties of the circuitry for applying current (the force electrode) are different from the properties of the circuitry for measuring the voltage (the sense electrodes). According to various implementations, there are two different sets of electrodes (force electrodes and sense electrodes), and each electrode has a positive and a negative side.

Using the four electrodes, different parts of the tissue, and tissue at varying depths can be scanned by adjusting the frequency of the injected waveform. Impedance is measured on a single vector without spatial resolution. In some implementations, more than four electrodes are used, and additional electrode pairs add multiple vectors, which add additional tissue scans. In some implementations, each pair of sense and force electrodes is one side of multiple vectors. For example, two pairs of sense and force electrodes form one vector, and three pairs of sense and force electrodes form three vectors. In other examples, more pairs of electrodes are used and more vectors are formed. As such, each vector monitors a selected spatial area.

The measurement of impedance can be used to determine physiologic information, including respiration rate, tidal volume, and lung fluids. Impedance measurements can also be used to determine derived metrics such as pulmonary resistance and lung fluid location. For respiration rate, the respiration of a patient causes air to go into the lungs and increase the lung volume which compresses the surrounding tissue. This leads to changes in the impedance with an increase on some vectors (mainly vectors that cross the lung(s)) and a decrease in other vectors other due to redirection of the current. Respiration rate is determined based on the changes in impedance, which follow the same periodicity as the respiration. Additionally, tidal volume can be monitored by determining the amplitude of the changes, which are proportional to the tidal volume (change in lung volume). The shape of the waveform relates to the breathing pattern and can be used to monitor the airway/lung resistance.

Fluid in the lungs can be detected and/or monitored by scanning multiple frequencies and/or multiple spatial vectors, which are used to distinguish fluids in the lung vs. other bodily fluids. Another method to add to the specificity of the separation between lung fluid and other bodily fluids is to measure impedance changes with posture. Changes in posture can cause lung fluids to move with gravity. The movement in fluids is detected by various vector measurements and helps separate the moving lung fluids from other bodily fluids. In one example, the vector of impedance is measured at the bottom of the lungs using a single frequency of 50 KHz. For example, the impedance vector between electrodes 114*c* and 114*d* of FIG. 1 may be measured. If the impedance vector is measured when the person is supine (horizontal position) and then is measured again after the patient moves to the standard Fowler position, a change in the impedance of 1 ohm or more can indicate the presence of fluid in the lungs. In congestive heart failure patients, the change in impedance is typically more than 5 ohms when patients start experiencing symptoms.

Note that in medicine, Fowler's position is a standard patient position in which the patient is seated in a semi-upright sitting position with the patient's torso at an angle relative to the horizontal plane. In various examples, Fowler's position includes the patient's torso being at an angle of between about 15 and thirty degrees, the patient's torso being at an angle of between about 30 and about 45 degrees, the patient's torso being at an angle of between about 45 and about 60 degrees, and the patient's torso being an angle of between about 60 and about 90 degrees. In standard Fowler's position, the patient's torso is between about 45 and about 60 degrees.

In various implementations, the device includes a sensor that can determine the position of the device, thereby indicating the horizontal position of the patient, including whether the patient is upright or supine. The device automatically measures thoracic impedance in both upright and supine positions of the patient and uses these two measurements to monitor and/or detect CHF.

As discussed above, the device also includes an electrocardiogram (ECG) measurement module 214, which can perform ECG measurements at some or all of the plurality of surface electrodes 114*a*-114*d* that make contact with the skin of the human subject 104 on his or her torso, upper chest, and/or neck areas. In one embodiment, the pulse oximetry measurement module 222 (or the finger-pocket device for performing finger-based pulse oximetry measurements) can be employed in conjunction with the ECG measurement module 214 to obtain further measurements.

Because respiratory activity can cause corresponding changes in the measured thoracic impedance, each of the breath rate measurement module 216 and the tidal volume measurement module 218 can operate in conjunction with the thoracic impedance measurement module 212 to obtain measurements of the human subject's breath rate/breath rate variability and tidal volume, respectively.

The heart sounds-based measurement module 220 can include an electronic stethoscope, stethophone, or any other suitable device for obtaining heart rate variability data, as well as obtaining and converting heart sounds (e.g., the S1 heart sound, "lub"; the S2 heart sound, "dub") to sensing data that can be subsequently algorithmically analyzed by the data analyzer 226 to obtain information pertaining to the S3 heart sound (also known as the proto-diastolic or ventricular gallop) which may be heard at the beginning of diastole, during the rapid filling of the ventricles, and the S4 heart sound (also known as the atrial gallop) which may heard late in diastole. In one implementation, the heart sounds-based measurement module 220 measures sub-audible heart sounds (heart sounds below about 40 Hz), thereby measuring S3 and S4 heart sounds that cannot be heard by a physician or other health care professional using a stethoscope. S3 and S4 heart sounds are pathological and indicate heart failure. Information about sub-audible S3 and S4 heart sounds can be used to detect and monitor CHF. The heart sounds can be measured by a sensor placed over the heart region. The sensor detects sounds and/or vibrations. The sensor detects different heart sounds depending on the location of sensor placement relative to the various regions of the heart. For example, to maximize the chances of detecting the signal that is pertinent to S3, the sensor is positioned over the apex of the heart, which is in the fifth intercostal space. Abnormal S3 heart sounds occur when the heart pumping is compromised. The S3 heart sounds are early indicators of heart problems and can change prior to other measureable heart signals. Because the S3 heart sounds have a lot of energy at low frequencies that are not audible to the human ear, the S3 heart sounds are initially undetectable by physicians. A sensing system sensitive to low frequencies coupled with an automated algorithm can detect the S3 heart sounds earlier. Any presence of S3 or S4 heart sounds in adult patients is abnormal and the detection of any energy that is determined to be S3 or S4 can be used to flag a potential problem. The flags from different sensors can be combined by a higher level logic to generate a single metric that can be designed to be more specific and more sensitive than individual measures.

In one embodiment, the pulse oximetry measurement module 222 (or the finger-pocket device for performing finger-based pulse oximetry measurements) can be employed in conjunction with the heart sounds-based measurement module 220 to obtain further measurements. It is noted that the pulse oximetry measurement module 222 can perform reflective or finger-based pulse oximetry measurements. In one embodiment, the pulse oximetry measurement module 222 can include a pulse rate sensor, as well as a blood oxygen level ($SpO_2$) sensor.

Having performed the thoracic impedance measurements, the ECG measurements, the breath rate and tidal volume measurements, the heart rate variability/heart sounds-based measurements, and the pulse oximetry measurements, the thoracic impedance measurement module 212, the electrocardiogram (ECG) measurement module 214, the breath rate and tidal volume measurement modules 216, 218, the heart sounds-based measurement module 220, and the pulse oximetry measurement module 222 provide corresponding multi-modality sensing data to the data analyzer 226 for at least partial data analysis, data trending, and/or data reduction. In one embodiment, such multi-modality sensing data can also be analyzed, trended, and/or reduced "in the cloud" and made available in cloud-based data storage 110 with pre-set alerts for use in various levels of clinical interventions. For example, the data analyzer 226 can (1) analyze the thoracic impedance measurement data to obtain information pertaining to the human subject's lung congestion, (2) analyze the breath rate and tidal volume measurement data to obtain information pertaining to the human subject's shortness of breath (e.g., dyspnea, paroxysmal nocturnal dyspnea), (3) analyze the ECG measurement data and heart rate variability data in multiple (e.g., 3) projections to obtain information pertaining to possible atrial fibrillation and localization in the human subject 104, and (4) analyze the heart sounds-based measurement data to obtain information pertaining to a possible increase in the S3 heart sound (which can be indicative of a failing left ventricle due to a dilated CHF condition).

The data analyzer 226 provides the at least partially analyzed multi-modality sensing data to the data fusion/decision engine 228, which effectively at least partially fuses or combines the multi-modality sensing data, in accordance with one or more algorithms and/or decision criteria, for subsequent use in making one or more inferences about the CHF status of the human subject 104. For example, combined multi-modality sensing data that show, substantially concurrently, an increase in the S3 heart sound, an increase in rapid shallow breathing while the human subject 104 is at rest, a decrease in the relative tidal volume, and a decrease in the thoracic impedance, can be a strong predictor of a potentially problematic CHF condition in the human subject 104. In one embodiment, such algorithms and/or decision criteria implemented in the data fusion/decision engine 228 can be proven and/or refined through one or more clinical trials for strengthening the inferences made by the data fusion/decision engine 228 regarding the human subject's CHF status. The processor 202 then provides the at least partially combined multi-modality sensing data to the transmitter/receiver 204, which transmits the combined multi-modality sensing data either directly over the wireless communication paths 122 to the cloud 110, or over the wireless communication paths 116 to the smartphone 106. Next, the smartphone 106 can transmit, via the communications network 108, the combined multi-modality sensing data over the wireless communication paths 118, 120 to the cloud 110, where it can be further analyzed, trended, reduced, and/or fused. The resulting curated multi-modality sensing data can then be remotely downloaded by hospital clinicians for monitoring and/or tracking purposes.

Figure 3A:
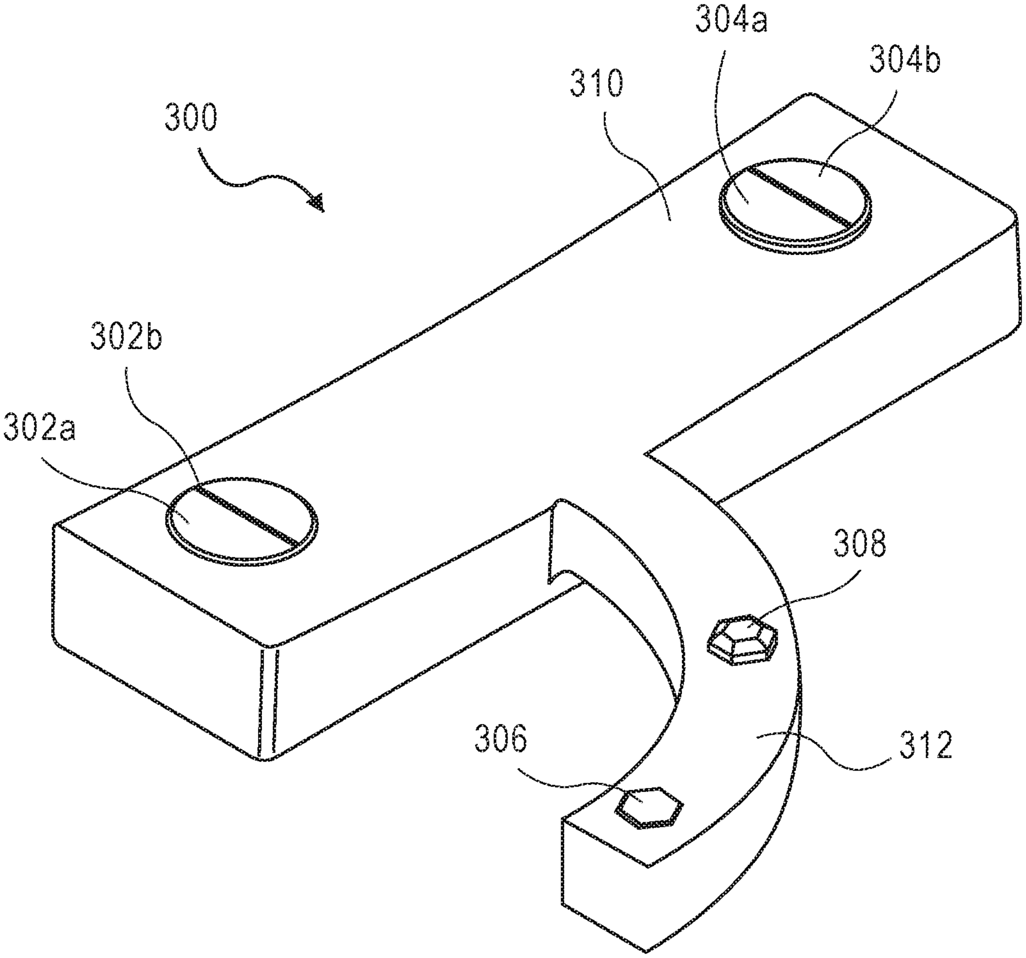
FIGS. 3A-3C are diagrams illustrating a device for detecting and monitoring health conditions in a subject, according to some embodiments of the disclosure.

FIG. 3A is a diagram illustrating a device 300 for detecting and monitoring health conditions in a subject, according to some embodiments of the disclosure. In particular, the device 300 non-invasively detects and monitors CHF conditions in human subjects. The device 300 includes a first electrode pair 302*a*-302*b*, a second electrode pair 304*a*-304*b*, a third electrode 306, and a fourth electrode 308. The first electrode pair 302*a*-302*b* includes one force electrode and one sense electrode, as described above. Similarly, the second electrode pair 304*a*-304*b* includes one force electrode and one sense electrode. The third 306 and fourth 308 electrode can be any type of electrode, including, for example, one of a heart sound sensor, a force electrode and, a sense electrode. The device 300 has an elongated rectangular base portion 310, which includes the first electrode pair 302*a*-302*b* positioned on a first end and the second electrode pair 304*a*-304*b* positioned on a second end. In various examples, the elongated base portion 310 is between about 10 cm and about 20 cm, and between about 2 cm and about 6 cm wide. In some examples, the elongated base portion 310 is between about 1 cm and about 4 cm thick. Along the mid-section of the length of the rectangular base portion 310, a curved tail portion 312 extends out in the same plane as the rectangular base portion 310 and arcs around toward the direction of the first electrode pair 302*a*-302*b*. The curved tail portion 312 includes the third electrode 306 and the fourth electrode 308. The third electrode 306 is positioned at the end of the curved tail portion 312 and the fourth electrode 308 is positioned in the middle of the curved tail portion 312. According to various implementations, the device 300 is placed on a subject's torso, with the electrodes 302*a*-302*b*, 304*a*-304*b*, 306, 308 in contact with the subject's skin.

Figure 3C:
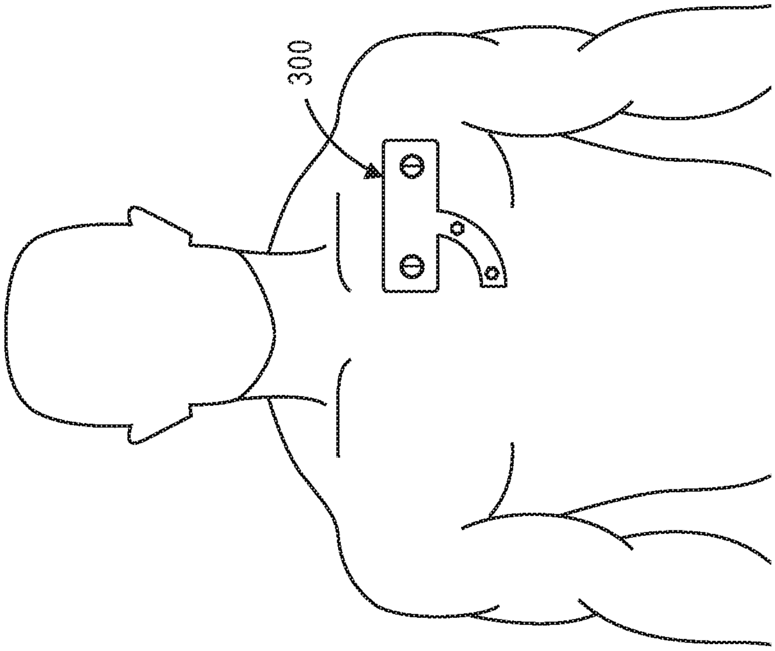
Figure 3B:
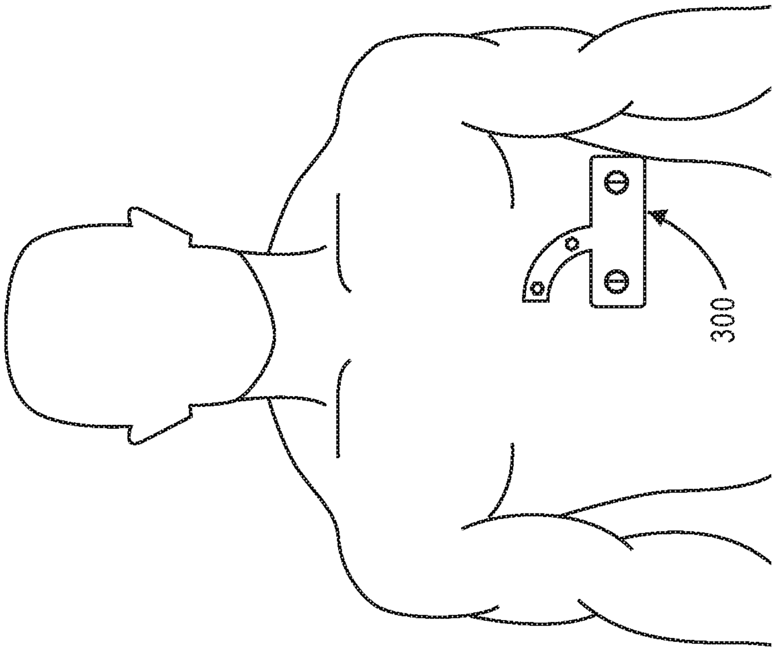

FIG. 3B shows the device 300 positioned on the torso of a subject. The elongated base portion 310 is positioned around the sixth intercostal space, and the curved tail portion 312 extends upwards, curving inward toward the midline of the torso, in some implementations, the fourth electrode 308 is positioned in the fifth intercostal space on the left side of the torso, and is optimally positioned to detect S3 sounds. In other implementations, the curved tail portion 312 curves outward away from the midline of the torso, FIG. 3C shows the device 300 positioned on the torso of a subject. The elongated base portion 310 is positioned below the shoulder level, and the curved tail portion 312 extends downwards over the heart, curving inward toward the midline of the torso. In other implementations, the curved tail portion 312 curves outward away from the midline of the torso.

Figure 4:
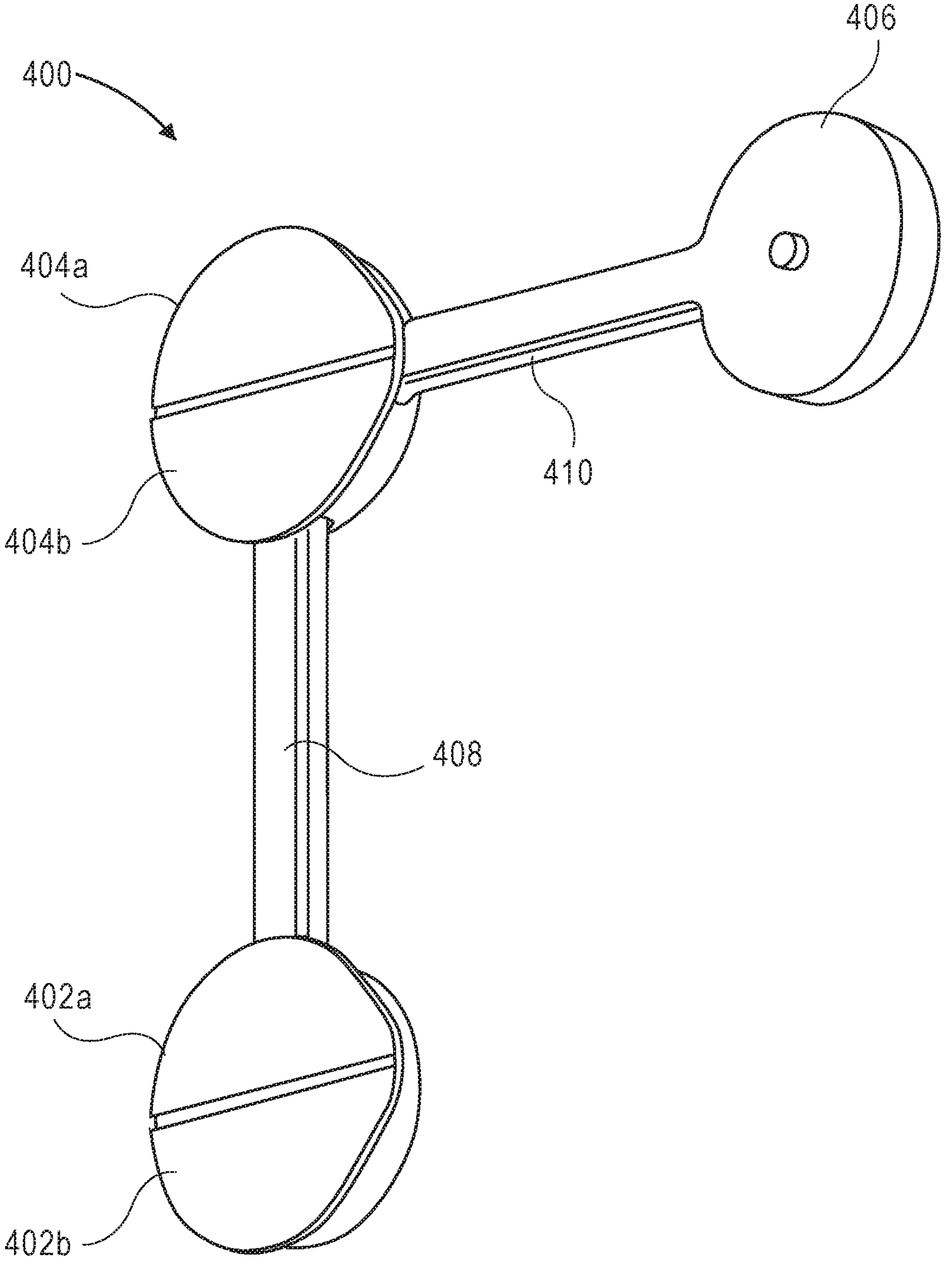
FIG. 4 is a diagram illustrating another device for detecting and monitoring health conditions in a subject, according to some embodiments of the disclosure.

FIG. 4 is a diagram illustrating a device 400 for detecting and monitoring health conditions in a subject, according to some embodiments of the disclosure. In particular, the device 400 non-invasively detects and monitors CHF conditions in human subjects. The device 400 includes a first electrode pair 402*a*-402*b*, a second electrode pair 404*a*-404*b*, and a sensor 406. The first electrode pair 402*a*-402*b* includes a force electrode and a sense electrode. Similarly, the second electrode pair 404*a*-404*b* includes a force electrode and a sense electrode. Additionally, one of the first electrode pair 402*a*-402*b* and one of the second electrode pair 404*a*-404*b* measures ECG. The sensor 406 is a heart sounds sensor for detecting sound vibrations. In one implementation, the sensor 406 is a piezo electric microphone. The membrane of the microphone protrudes to contact the torso and detect the heart sounds. The first electrode pair 402*a*-402*b* is connected to the second electrode pair 404*a*-404*b* via a first elongated element 408. The second electrode pair 404*a*-404*b* is connected to the sensor 406 via a second elongated element 410. As shown in FIG. 4, in the device 400, the first 408 and second 410 elongated elements are approximately perpendicular to each other. In other implementations, the first 408 and second 410 elongated elements can be oriented at any selected position relative to each other. The device 400 is placed on a subject's torso, with the electrodes 402*a*-402*b* and 404*a*-404*b*, and the sensor 406 in contact with the subject's skin. In some implementations, the electrodes 402*a*-402*b* and 404*a*-404*b*, are positioned along the sixth intercostal space and the sensor 406 is positioned along the fifth intercostal space at the apex of the heart.

Figure 5:
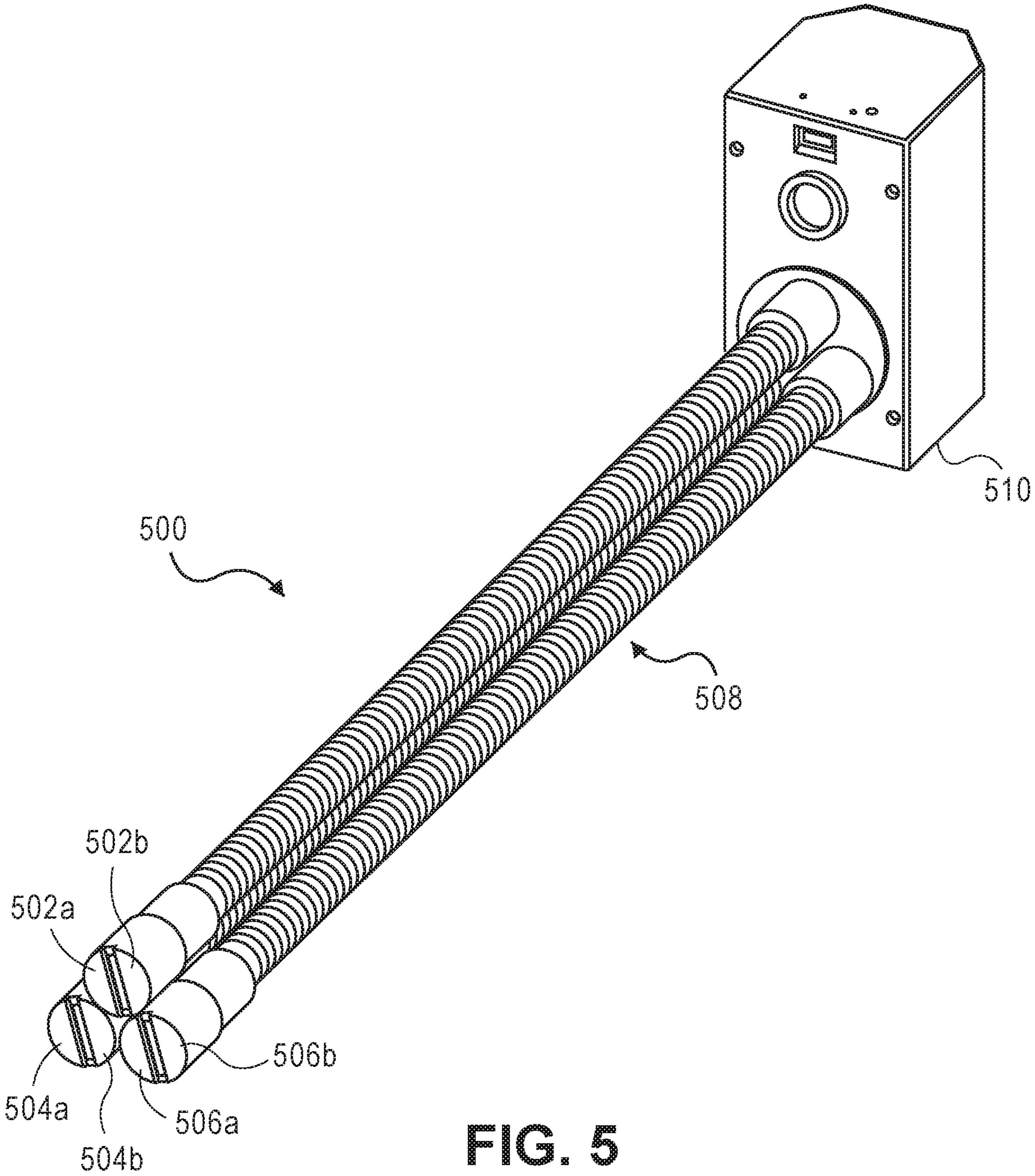
FIG. 5 is a diagram illustrating another device for detecting and monitoring health conditions in a subject, according to some embodiments of the disclosure.

FIG. 5 is a diagram illustrating a device 500 for detecting and monitoring health conditions in a subject, according to some embodiments of the disclosure. The device 500 includes three long flexible arms 508 that extend from a rectangular box 510. At the tip of each of the flexible arms 508 is a pair electrodes—first electrode pair 502*a*-502*b*, second electrode pair 504*a*-504*b*, and third electrode pair 506*a*-506*b*. The electrode pair 502*a*-502*b*, 504*a*-504*b*, 506*a*-506*b* can be moved to be oriented to fit a subject's body and secured in place. The device 500 is a handheld device that the subject places on the body. In some examples, the subject positions the device 500 on the body regularly, such as two or more times per day, and records measurements. According to some implementations, the device 500 includes a sensor for recording heart sounds. The heart sound sensor may also be attached to the device via a long flexible arm. The heart sound sensor may be a microphone, and in some examples it is a piezo electric microphone.

In other implementations, electrodes and/or other sensors are positioned subcutaneously on a subject Subcutaneous sensors can remain in place long term and can be connected to an external device for measurements. In other implementations, electrodes and/or other sensors are positioned within patches which attach to a subject's skin. The patches are connected to an external device for measurement.

Figure 6:
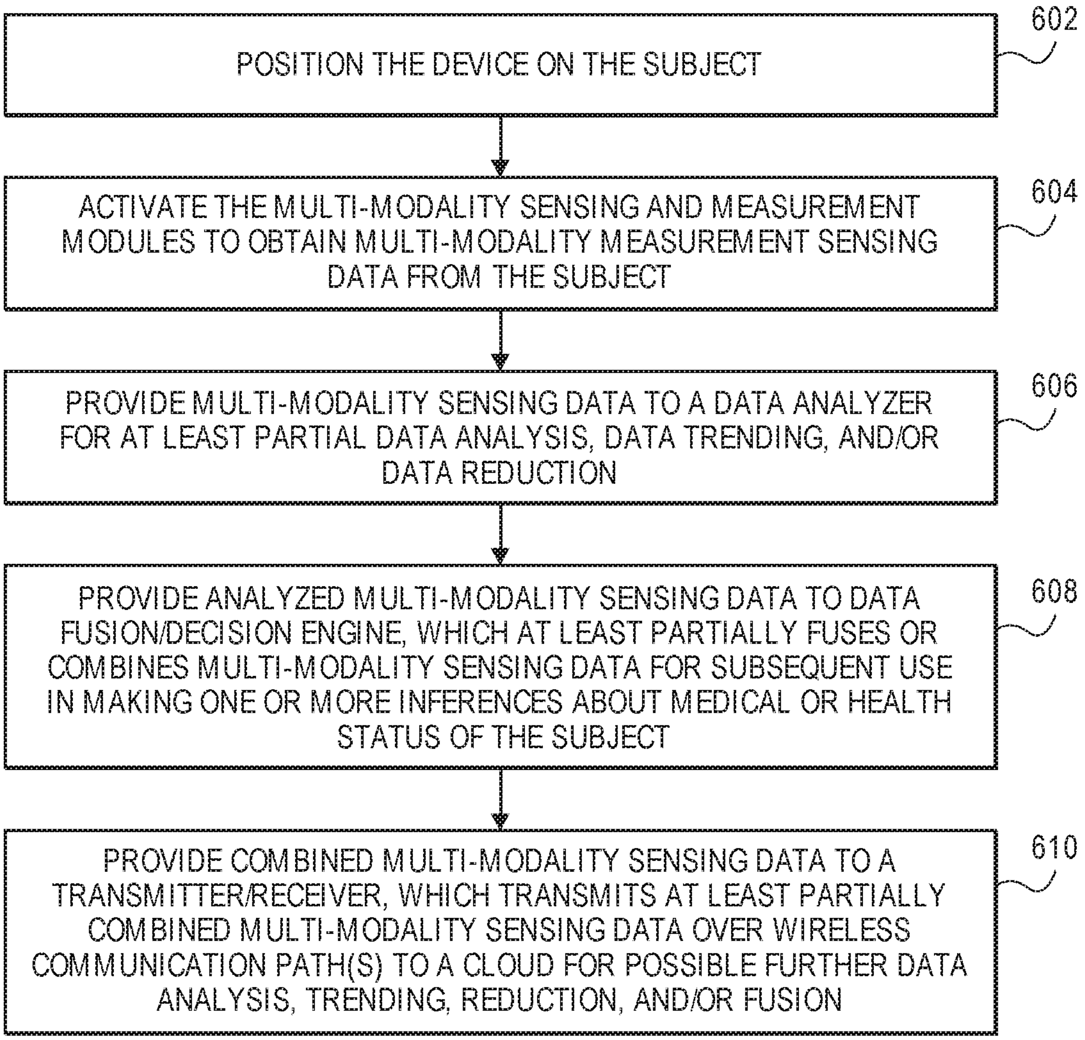
FIG. 6 is a flow diagram illustrating an exemplary method of detecting the onset of a medical or health condition and/or monitoring its severity, according to some embodiments of the disclosure.

An exemplary method of non-invasively detecting and monitoring medical or health conditions in human subjects using multiple modalities of sensing is described below with reference to FIG. 6, as well as FIGS. 1 and 2. At block 602, the system 102 (see FIGS. 1 and 2), configured as a suitably shaped device, is positioned on the human subject 104 such that it makes contact with suitable parts or areas of the body via at least the plurality of surface electrodes/sensors 114*a*-114*d*. At block 604, once the system 102 is positioned in contact with the suitable parts or areas of the body, the plurality of multi-modality sensing and measurement modules 112 are activated to obtain multi-modality sensing data from the human subject 104, including, but not limited to, one or more of thoracic impedance sensing data, ECG sensing data, breath rate and tidal volume sensing data, heart rate variability/heart sounds-based sensing data, and pulse oximetry sensing data. At block 306, the multi-modality sensing data are provided to the data analyzer 226 for at least partial data analysis, data trending, and/or data reduction. At block 608, the analyzed multi-modality sensing data are provided to the data fusion/decision engine 228, which effectively at least partially fuses or combines the multi-modality sensing data for subsequent use in making one or more inferences about the medical or health status of the human subject 104. At block 610, the combined multi-modality sensing data are provided to the transmitter/receiver 204, which transmits the at least partially combined multi-modality sensing data over the wireless communication paths 122 to the cloud 110 for possible further data analysis, trending, reduction, and/or fusion. The partially combined multi-modality sensing data can also be transmitted over the wireless communication paths 122 to the cloud 110 for remote downloading by hospital clinicians for monitoring and/or tracking purposes.

Figure 7:
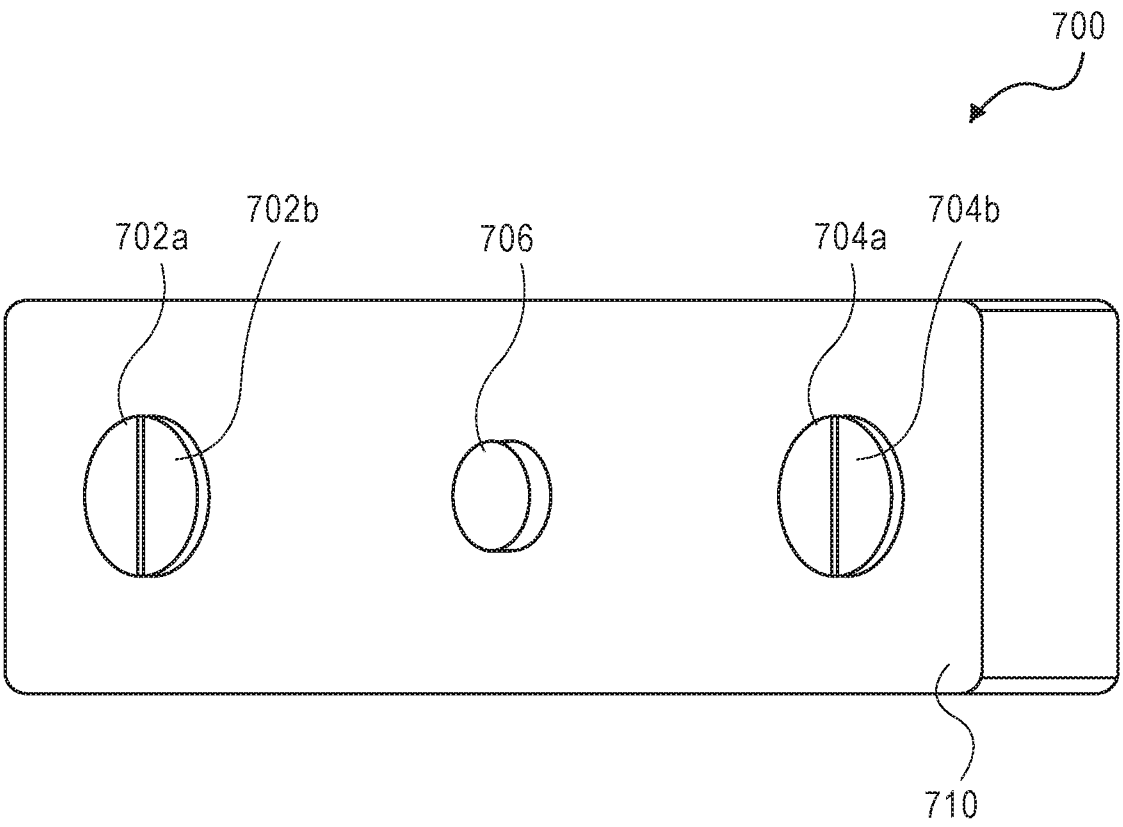
FIG. 7 is a diagram illustrating another device for detecting and monitoring health conditions in a subject, according to some embodiments of the disclosure.

FIG. 7 is a diagram illustrating a device 700 for detecting and monitoring health conditions in a subject, according to some embodiments of the disclosure. In particular, the device 700 non-invasively detects and monitors COPD conditions in human subjects. The device 700 is an elongated rectangular element 704 and includes first 702*a*, second 702*b*, and third 702*c* electrodes. The first electrode 702*a* is positioned at a first end of the elongated rectangular element 704, the second electrode 702*b* is positioned approximately in the center of the elongated rectangular element 704, and the third electrode 702*c* is positioned at a second end of the elongated rectangular element 704. In use, the device 700 is positioned on the torso of a subject with the electrodes 702*a*-702*c* positioned in contact with the subject's skin. As described above with respect to the system 102 of FIG. 1, data from the electrodes 702*a*-702*c* are connected to a plurality of multi-modality sensing and measurement modules (such as the modules 112 shown in FIG. 2), which can be activated to gather, collect, sense, measure, or otherwise obtain multi-modality sensing data from the subject.

To detect and/or monitor for COPD, the heart sounds sensor is positioned higher on the torso for better detection of lung sounds. Measurements for COPD include impedance for determining respiration rate, ECG if desired, impedance for determining tidal volume, lung sounds (for detection of abnormal lung rails), and impedance for measuring the shape of the lung volume changes. In particular, the change in the shape of the impedance variations indicates the lung/airway resistance, which can be used to determine the presence of COPD.

Figure 8A:
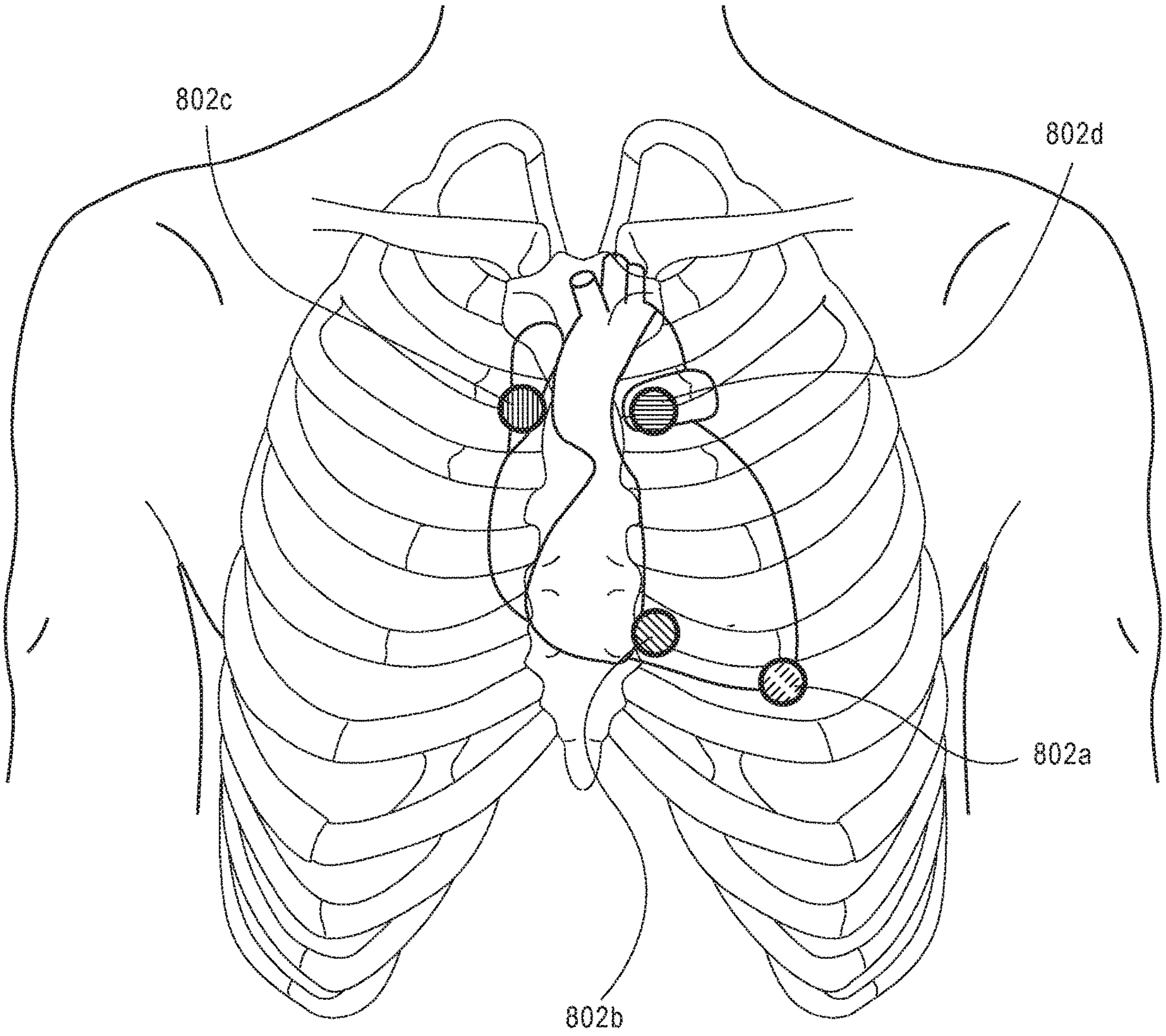
FIGS. 8A-8E are diagrams illustrating various examples of electrode and sensor torso placements for detecting and monitoring health conditions in a subject, according to some embodiments of the disclosure.

FIGS. 8A-8E are diagrams illustrating various examples of electrode and sensor torso placements for detecting and monitoring health conditions in a subject, according to some embodiments of the disclosure. In FIG. 8A, four elements 802*a*-802*d* are positioned on the torso of the subject, generally over the subject's heart. One element 802*a* is positioned at the apex of the heart, in the fifth intercostal space. According to some examples, the placement of 802*a* at the apex of the heart in the fifth intercostal space is generally optimal for detection of S3 and S4 heart sounds.

Figure 8C:
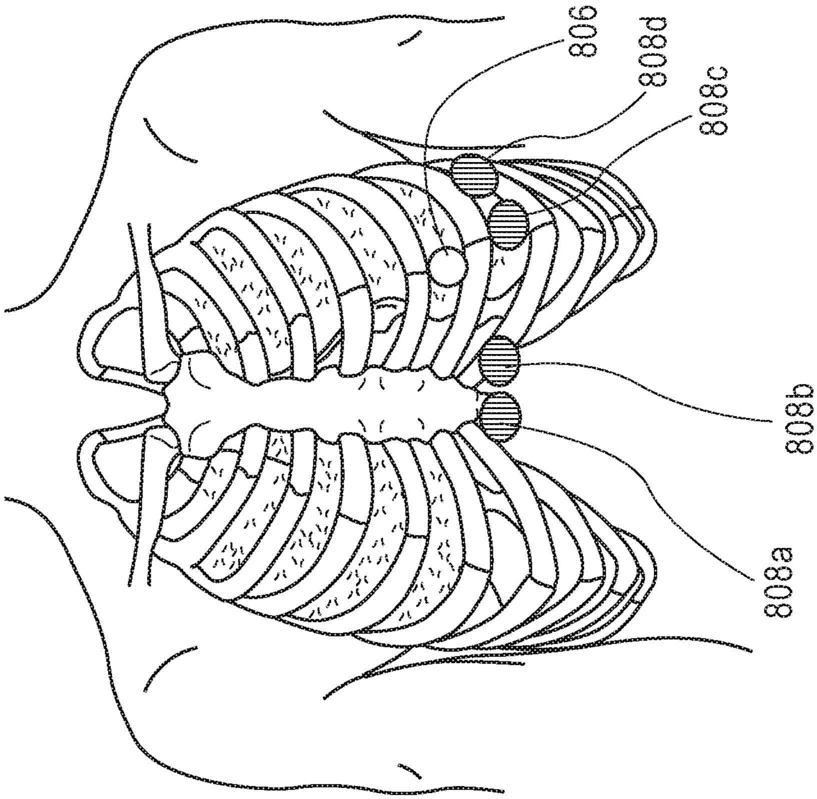
Figure 8B:
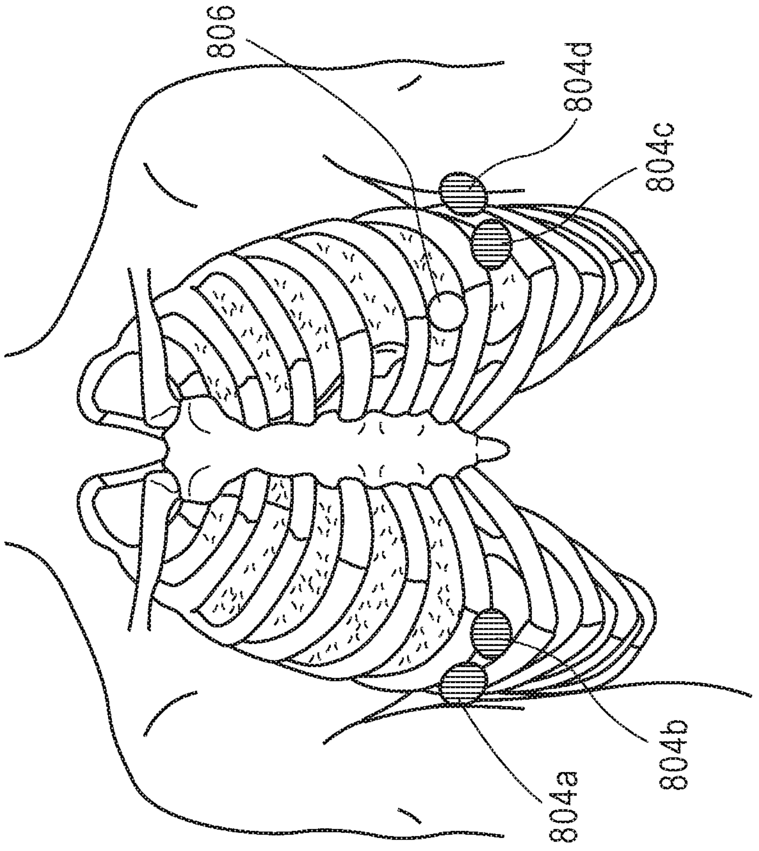

In FIG. 8B, elements 804*a*-804*d* are positioned across both sides of the torso, and are thereby positioned to measure the impedance across both lungs. The element 806 is a microphone for detecting heart sounds. A device including elements 804*a*-804*d* extends across the width of the torso. In some implementations it may be secured in place with a strap around the torso. The elements 804*a*-804*d* can also be used to measure an ECG.

In FIG. 8C, elements 808*a*-808*d* are positioned on one side of the torso and measure the impedance across one lung. The element 806 is a microphone for detecting heart sounds. A device including elements 808*a*-808*d* extends across one side of the torso. In one example, a device such as the device 300 in FIG. 3A can include elements 808*a*-808*d* and 806. The elements 808*a*-808*d* can also he used to measure an ECG.

Figure 8D:
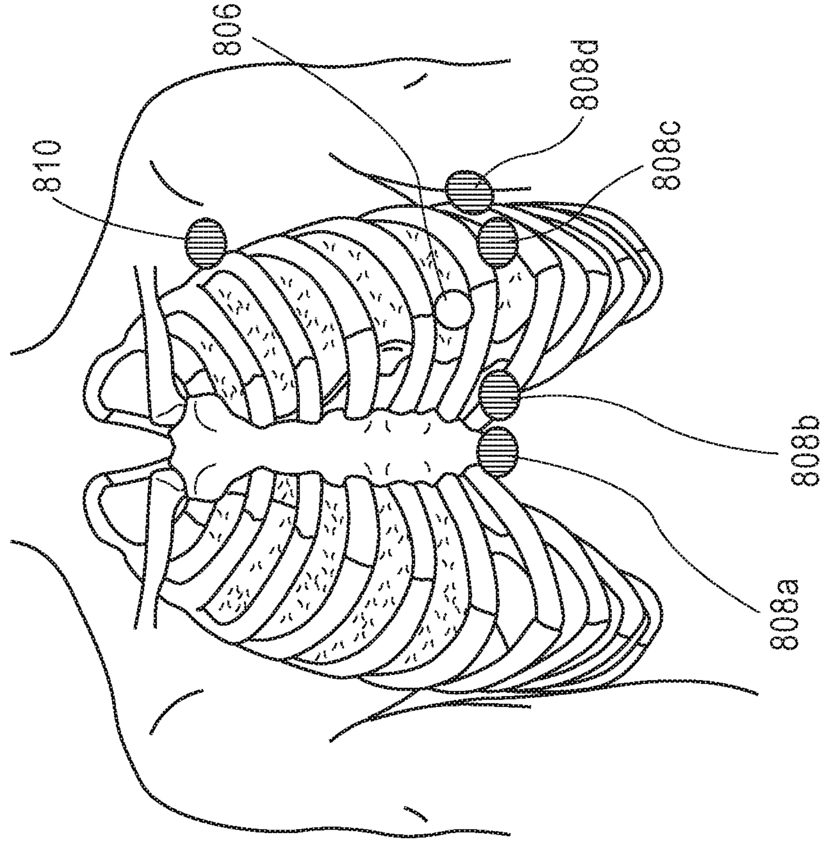

FIG. 8D shows the elements 808*a*-808*d* and 806 of FIG. 8C, and an additional element 810. The element 810 can be used with any of the elements 808*a*-808*d* to measure an ECG.

Figure 8E:
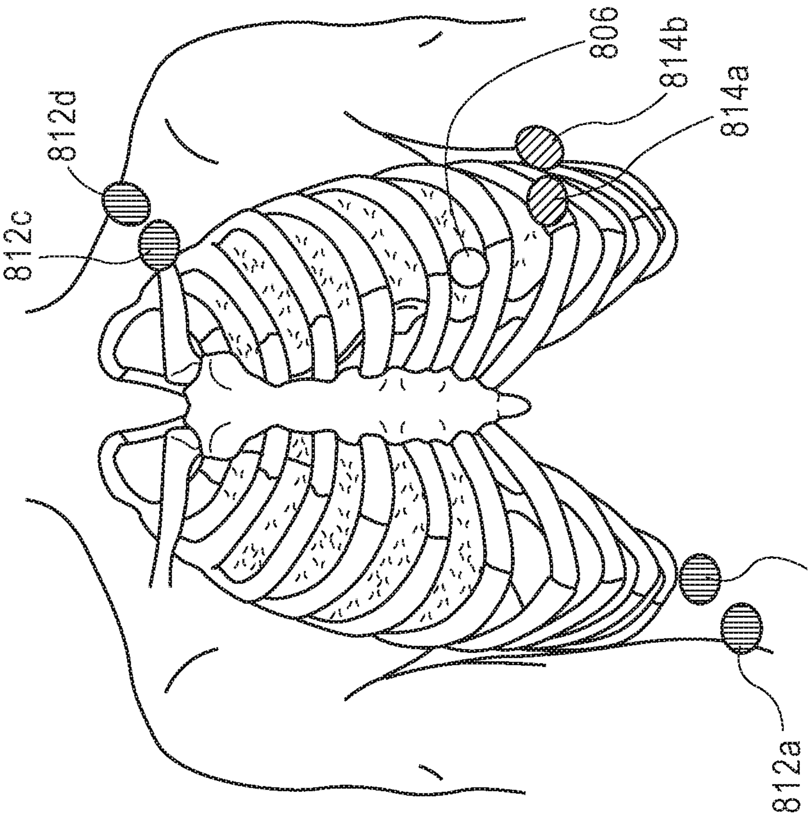

FIG. 8E shows elements 812*a*-812*d*. 814*a*-814*b*, and 806. Elements 812*a*-812*d* and 814*a*-814*b* can be used to measure impedance and to measure an ECG. The configuration of elements 812*a*-812*d*, 814*a*-814*b* and 806 can be implemented in a device such as a vest or a shirt.

Having described the above illustrative embodiments of systems, apparatus, and methods of non-invasively detecting and monitoring medical or health conditions such as CHF conditions in human subjects using multiple modalities of sensing, other alternative embodiments and/or variations can be made and/or practiced. For example, it was described herein that the thoracic impedance measurement module 212, the ECG measurement module 214, the breath rate and tidal volume measurement modules 216, 218, the heart sounds-based measurement module 220, and the pulse oximetry measurement module 222 can provide corresponding multi-modality sensing data to the data analyzer 226 for subsequent data analysis, data trending, and/or data reduction. In an alternative embodiment, one or more of the plurality of multi-modality sensing and measurement modules 112 can further obtain multi-modality sensing data pertaining to non-invasive, pressure wave velocity (PWV)-based systolic and/or diastolic blood pressures between the human subject's chest and finger, for example, and/or cardiac output data based on the direct measurement of at least the cardiac contractility, and provide these additional modalities of sensing data to the data analyzer 226 for further data analysis, data trending, and/or data reduction.

It will be appreciated by those of ordinary skill in the art that modifications to and variations of the above-described systems, apparatus, and methods may be made without departing from the inventive concepts disclosed herein. Accordingly, the present application should not be viewed as limited except as by the scope and spirit of the appended summary of important aspects.

Appendix

Figure 9A:
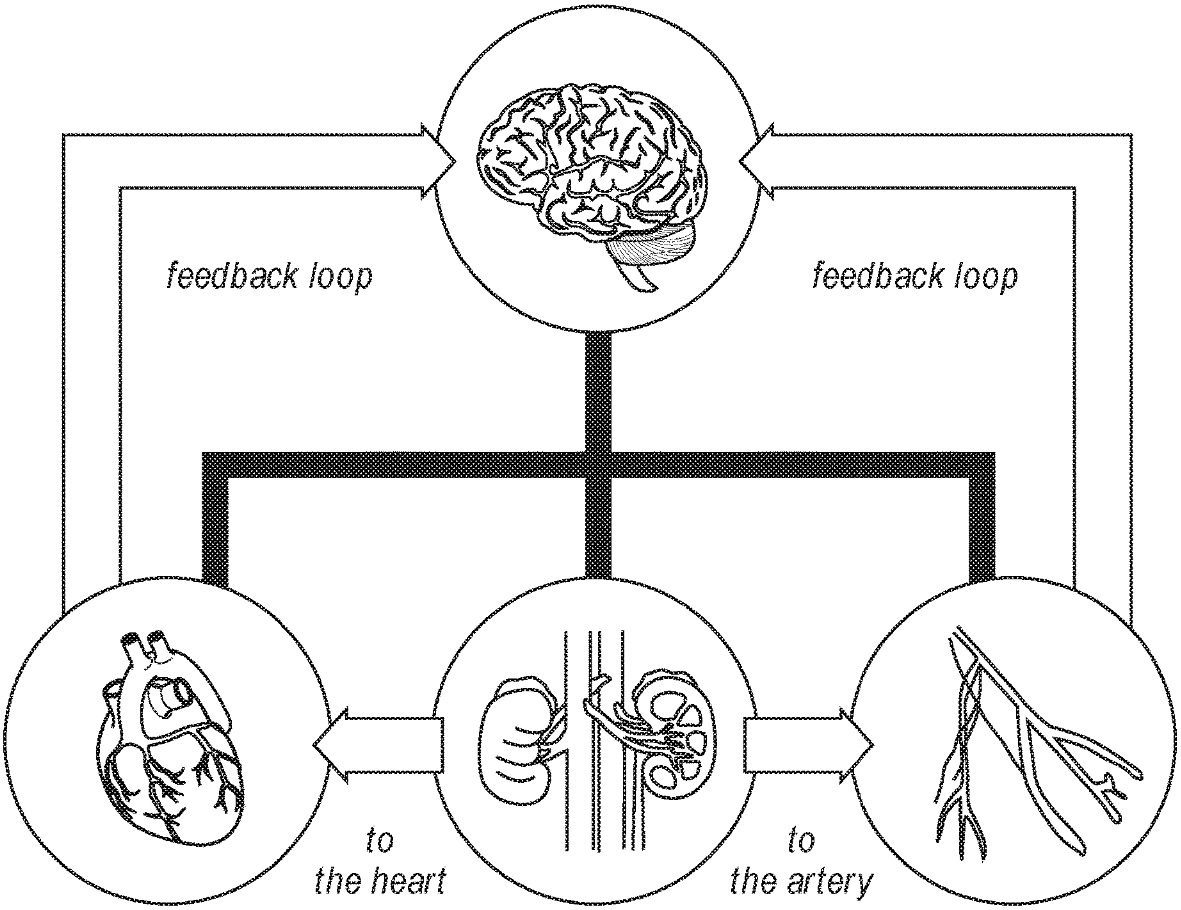
FIGS. 9A and 9B are diagrams illustrating an exemplary cardiovascular feedback loop.
Figure 9B:
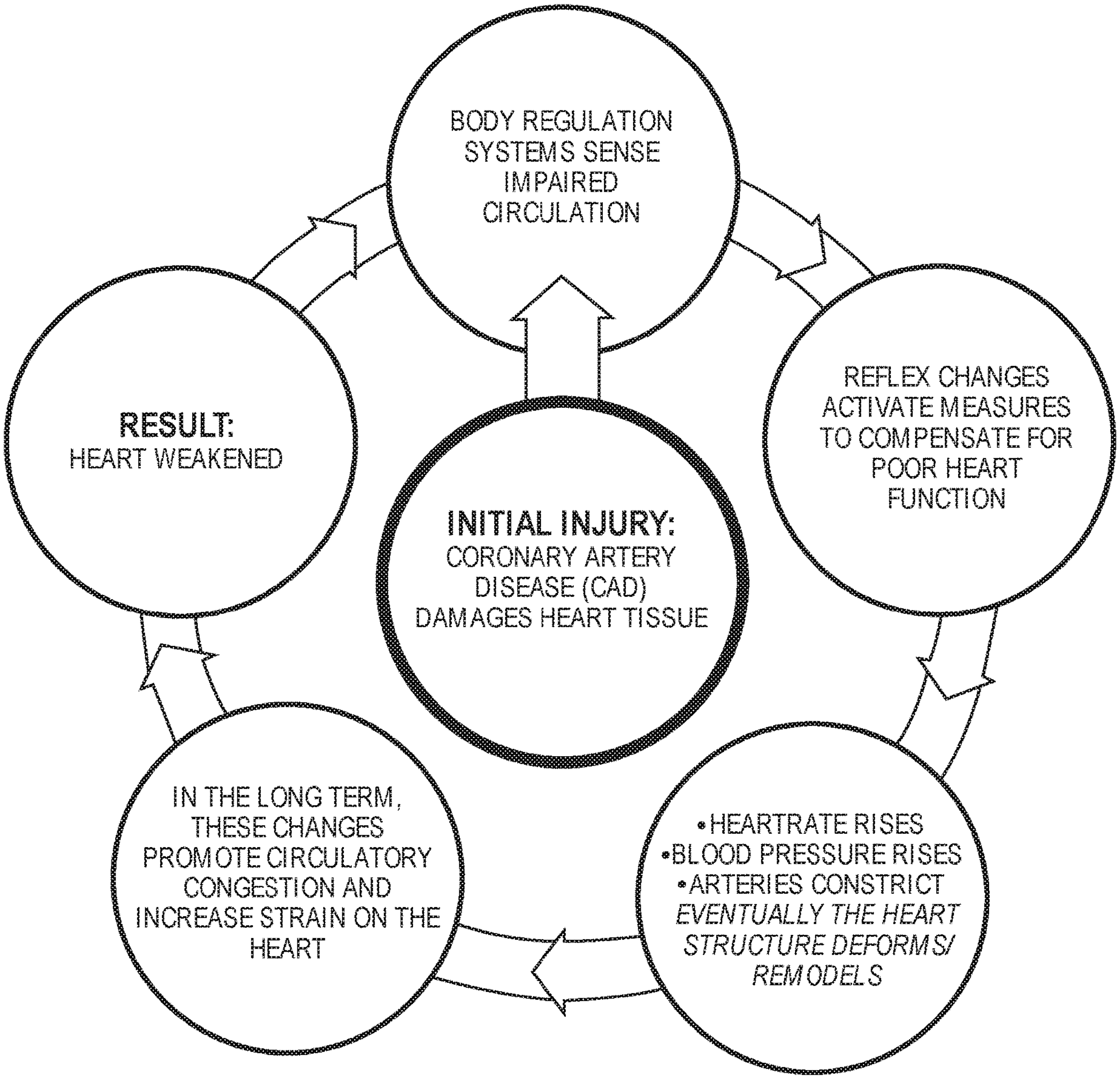

Cardiovascular Feedback Loop (See FIGS. 9A and 9B)

The nervous system receives a signal that blood pressure is falling. To ensure survival, the brain sends signals to the heart, kidneys, and arteries, each playing a role in diverting blood flow to major organs and maintaining blood pressure. In response to the signals from the brain, the heart beats faster and more forcefully. This increases the circulating blood pressure to the body. It then sends feedback to the brain, informing that changes have been made, and to halt the nervous system's intervention. The signals from the brain stimulate the adrenal glands (a member of the endocrine system located on top of each kidney) to secrete epinephrine (generally known as adrenaline) and norepinephrine into the bloodstream. Upon reaching target organs, it alters their activity. The arteries, in response to the signals from the brain, assist the blood pressure in the body by changing arterial resistance to flow. Changes in vascular tone shift blood away from muscles to internal organs, as their health most directly effects survival. Arteries send feedback to the brain, informing it of the changes.

Figure 10:
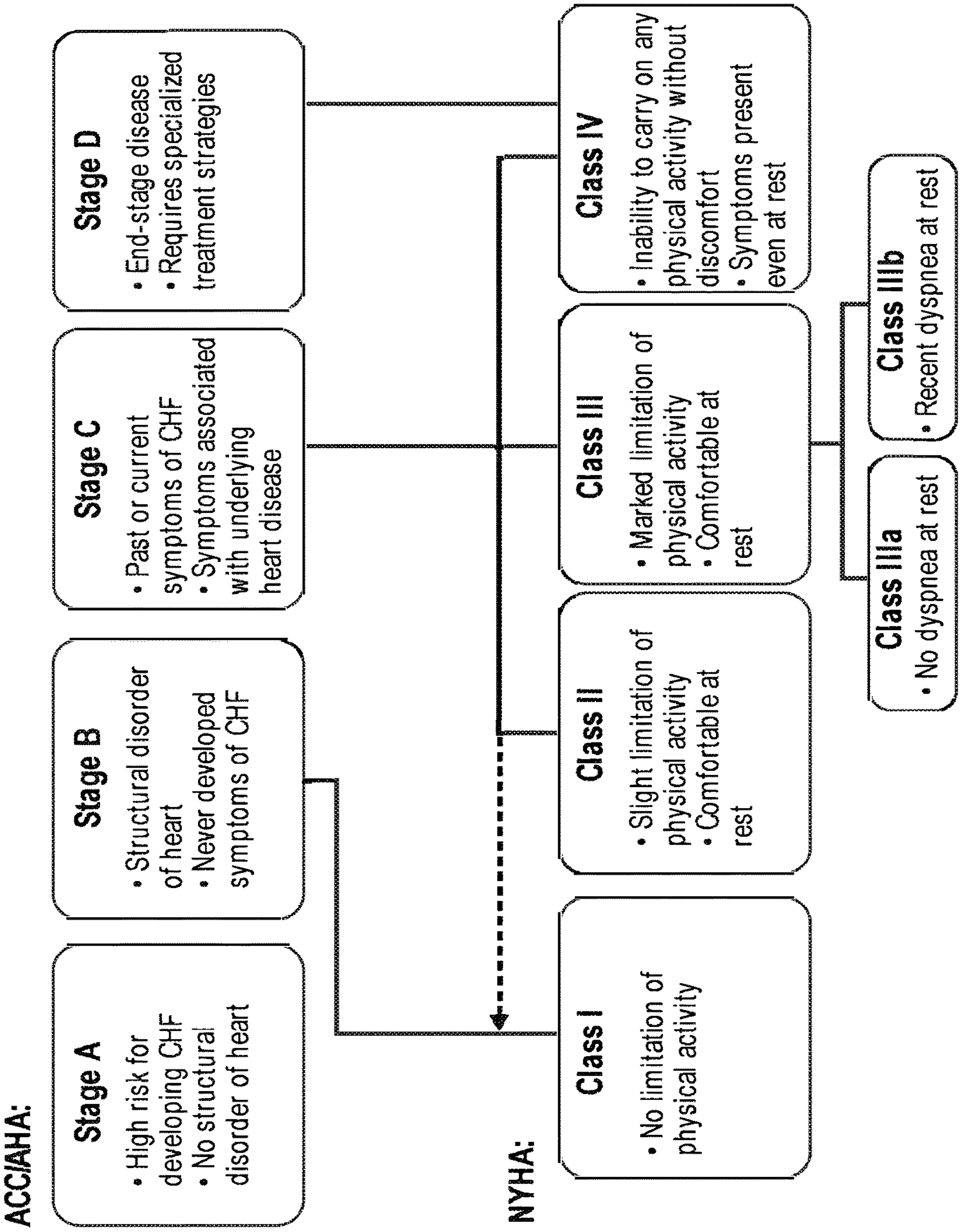
FIG. 10 is a diagram illustrating the medical classifications of heart failure.

What is "Heart Failure?" (see FIG. 10)

The 2013 ACCF/AHA Heart Failure Guidelines defined heart failure as "a complex clinical syndrome that results from any structural or functional impairment of ventricular filling or ejection of blood." Heart pump impairment resulting in symptoms:

Heart: It is necessary that any occurrence of clinical heart failure must include a primary or secondary involvement of the heart. If this is not evident, we either have not looked hard enough or it is not heart failure.

Pump: A complete description of the heart includes multiple functions including electrical, hormonal, and structural components. For heart failure to be present, however, there must be a manifest effect on the ability of the heart to move blood in the circulation.

Impairment: Impairment implies a degree of insufficiency that, in general, does not require complete replacement therapy. It may only be unmasked by activity or stress. If given a letter grade, many patients' heart function would rate a C+ rather than an F. Nevertheless, some degree of decreased function must be present for an individual to have heart failure, Resulting in: An initial insult to the heart may result in an immediate profound or a subtle progression to heart pump impairment only over time. Neurohormonal mechanisms may be activated and contribute to this syndrome. This may include adverse structural and biochemical remodeling. Any process affecting the heart must be causally related to an individual's status to result in heart failure.

Stages: The ACC/AHA classification of heart failure defines 4 stages of heart failure beginning with (1) risk factors for heart failure, (2) asymptomatic heart impairment, (3) symptomatic heart failure, and (4) advanced heart failure.

What is claimed is:

1. A device for non-invasively detecting and monitoring medical conditions, comprising:
- a first electrode pair configured to he positioned on a subject and further configured to measure a disturbance along a first vector;
- a second electrode pair configured to be positioned on the subject and further configured to measure a disturbance along a second vector;
- a sensor configured to be positioned on a torso of the subject and further configured to detect a change in an orientation of the device, the orientation of the device indicating an orientation of the torso of the subject; and
- a thoracic impedance measurement module coupled to the first electrode pair and the second electrode pair, wherein the thoracic impedance measurement module is configured to:
  - adjust a first frequency of a first current for performance of a first set of impedance measurements and a second frequency of a second current for performance of each impedance measurement of a second set of impedance measurements to scan varying depths of the subject,
  - determine the first set of impedance measurements at a first depth of the subject along the first vector and along the second vector when the device is in a first orientation, and
  - determine the second set of impedance measurements at a second depth of the subject along the first vector and along the second vector in response to detecting that the orientation of the device has changed from the first orientation to a second orientation,
  - wherein physiologic information for the subject is determined based on a change between the first set of impedance measurements and the second set of impedance measurements.

2. The device of claim 1, wherein:
- the first electrode pair includes:
  - a first force electrode configured to be positioned on the subject and further configured to apply a first current to the subject; and
  - a first sense electrode configured to be positioned on the subject and fixther configured to sense a disturbance along a first vector caused by the first current, wherein the first vector extends through the subject between the first force electrode and the first sense electrode; and
- the second electrode pair includes:
  - a second force electrode configured to be positioned on the subject and further configured to apply a second current to the subject; and
  - a second sense electrode configured to be positioned on the subject and further configured to sense a disturbance along a second vector caused by the second current, wherein the second vector extends through the subject between the second tbrce electrode and the second sense electrode.

3. The device of claim 1, wherein the physiologic information is related to lung fluid of the subject.

4. The device of claim 1, wherein the first electrode pair is configured to be positioned on the torso of the subject, wherein the first vector extends through the torso of the subject, wherein the second electrode pair is configured to be positioned on an upper chest of the subject, and wherein the second vector extends through the upper chest of the subject.

5. The device of claim 1, wherein the first set of impedance measurements comprises a first disturbance along the first vector, the first disturbance comprising a measured voltage along the first vector, and wherein the first set of impedance measurements further comprises a second disturbance along the second vector, the second disturbance comprising a measured voltage along the second vector.

6. The device of claim 1, further comprising an electrocardiogram (ECG) measurement module coupled to the first electrode pair, wherein the ECG measurement module utilizes the first electrode pair to perform ECG measurements.

7. The device of claim 1, further comprising:
- a heart sound sensor configured to be positioned over a heart region of the subject and further configured to detect one or more heart sounds of the subject; and
- a heart sounds-based measurement module coupled to the heart sound sensor, the heart sounds-based measurement module configured to convert the one or more heart sounds to sensing data for analysis.

8. The device of claim 7, further comprising a data fusion/decision engine coupled to the thoracic impedance measurement module and the heart sounds-based measurement module, the data fusion/decision engine configured to fuse a first impedance along the first vector, a second impedance along the second vector, and the sensing data for making one or more inferences about the subject.

9. A system for non-invasively detecting and monitoring medical conditions, comprising:
- a sensor configured to be positioned on a torso of a subject and further configured to detect a change in an orientation of the sensor, the orientation of the sensor indicating an orientation of the torso of the subject;
- a thoracic impedance measurement module configured to:
  - adjust a first frequency of a first current for performance of a first measurement of a first impedance and a second frequency of a second current for performance of a second measurement of a second impedance to scan varying depths of the subject;
  - determine the first impedance at a first depth along a first vector from a first force electrode configured to be positioned on the subject to a first sense electrode configured to be positioned on the subject; and
  - determine the second impedance at a second depth along a second vector from a second force electrode configured to be positioned on the subject to a second sense electrode configured to be positioned on the subject; and
- a data analyzer coupled to the thoracic impedance measurement module and the sensor, the data analyzer configured to perfbrrn data analysis, data trending, or data reduction with the first impedance along the first vector and the second impedance along the second vector, wherein the first impedance and the second impedance are measured when the sensor detects that the sensor is in a first orientation, and a third impedance along the first vector and a fourth impedance along the second vector, wherein the third impedance and the fourth impedance are measured in response to detecting that the orientation of the sensor has changed from a first orientation to a second orientation.

10. The system of claim 9, wherein the first force electrode and the, second sense electrode are configured to be positioned on the torso of the subject, wherein the first vector extends through the torso of the subject, wherein the second force electrode and the second sense electrode are configured to be positioned on an upper chest of the subject, and wherein the second vector extends through the upper chest of the subject.

11. The system of claim 9, further comprising a heart sounds-based measurement module coupled to the data analyzer, the heart sounds-based measurement module configured to convert one or more heart sounds received from a heart sound sensor to sensing data, and wherein the data analysis, the data trending, or the data reduction is further perforated with the sensing data.

12. The system of claim 11, further comprising a data fusion/decision engine coupled to the data analyzer, the data fusion/decision engine configured to:

receive results of the data analysis, the data trending, or the data reduction; and fuse the results for making inferences about the subject.

13. The system of claim 12, further including a processor, wherein the processor includes the data analyzer and the data fusion: decision engine.

14. The system of claim 12, further comprising a transmitter/receiver coupled to the data fusion/decision engine, the transmitter/receiver configured to transmit the fused results over one or more wireless communication paths to a remote device.

15. A method for non-invasively detecting and monitoring medical conditions, comprising:

determining, by a device having a sensor positioned on a torso of a subject and an electrode pair that is positioned on the subject, that the device is in a first orientation;

adjust a first frequency of a first current for performance of a first measurement of a first thoracic impedance;

determining, by the device, the first thoracic impedance at a first depth for the subject when the device is in the first orientation;

detecting, by the device, a change in an orientation of the device from the first orientation to a second orientation;

adjust a second frequency of a second current for performance of a second measurement of a second thoracic impedance to scan varying depths of the subject;

determining, by the device, the second thoracic impedance at a second depth for the subject when the device is in the second orientation; and determining, based on a change between the first thoracic impedance and the second thoracic impedance, physiologic information for the subject.

16. The method of claim 15, wherein:

determining the first thoracic impedance includes:

applying, by a force electrode of the electrode pair, the first current to the subject when the device is in the first orientation; and detecting, by a sense electrode of the electrode pair, a first disturbance caused by the first current being applied to the subject; and determining the second thoracic impedance includes:

applying, by the force electrode, the second current to the subject when the device is in the second orientation; and detecting, by the sense electrode, a second disturbance caused by the second current being applied to the subject.

17. The method of claim 16, wherein the first frequency has a magnitude between 50 kilohertz (kHz) and 100 kHz and the first current has an amplitude between 1 milliamps root mean squared (mARMs) and 4 $mA_R ms$, and wherein the second frequency has a magnitude between 50 kHz and 100 kHz and the second current has an amplitude between 1 mARms and 4 mARms.

18. The method of claim 15, wherein:

the first orientation comprises a wearer of the device being approximately horizontal; and the second orientation comprises a wearer of the device being in a Fowler's position.

19. The method of claim 18, wherein the second orientation comprises the wearer of the device being in standard Fowler's position.

* * * * *